US011253210B2

(12) United States Patent
Jones et al.

(10) Patent No.: US 11,253,210 B2
(45) Date of Patent: Feb. 22, 2022

(54) AUTOMATED TRACKING OF FIDUCIAL MARKER CLUSTERS IN X-RAY IMAGES

(71) Applicant: The Regents of the University of Colorado, a body corporate, Denver, CO (US)

(72) Inventors: Bernard Jones, Denver, CO (US); Warren Campbell, Denver, CO (US); Moyed Mitten, Greenwood Village, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 1132 days.

(21) Appl. No.: 15/662,925

(22) Filed: Jul. 28, 2017

(65) Prior Publication Data
US 2018/0028133 A1    Feb. 1, 2018

Related U.S. Application Data

(60) Provisional application No. 62/368,870, filed on Jul. 29, 2016.

(51) Int. Cl.
*A61B 5/05*    (2021.01)
*A61B 6/00*    (2006.01)
(Continued)

(52) U.S. Cl.
CPC .......... *A61B 6/4085* (2013.01); *A61B 6/583* (2013.01); *A61N 5/1049* (2013.01); *G06T 5/003* (2013.01);
(Continued)

(58) Field of Classification Search
CPC combination set(s) only.
See application file for complete search history.

(56) References Cited

U.S. PATENT DOCUMENTS

| 5,727,554 A | 3/1998 | Kalend et al. |
| 2009/0208074 A1* | 8/2009 | Wiersma ................. G06T 7/251 382/128 |

(Continued)

OTHER PUBLICATIONS

International Application No. PCT/US2017/044423, International Search Report and Written Opinion, 10 pages, dated Dec. 11, 2017.
Marchant, T. E. et al., "Automatic Tracking of Implanted Fiducial Markers in Cone Beam CT Projection Images," Medical Physics, vol. 39, No. 3, pp. 1322-1334, Mar. 2012.

*Primary Examiner* — Joel F Brutus

(57) ABSTRACT

Various embodiments of the present technology generally relate to identification of tumor location. More specifically, some embodiments of the present technology relate automated tracking of fiducial marker clusters in x-ray images for the real-time identification of tumor location and guidance of radiation therapy beams. Some embodiments use processed CBCT projection images, an automated routine of reconstruction, forward-projection, tracking, and stabilization generated static templates of the marker cluster at arbitrary viewing angles. Breathing data can be incorporated into some embodiments, resulting in dynamic templates dependent on both viewing angle and breathing motion. In some embodiments, marker clusters can be tracked using normalized cross correlations between templates (either static or dynamic) and CBCT projection images.

24 Claims, 14 Drawing Sheets

(51) Int. Cl.
  *G06T 7/00* (2017.01)
  *A61N 5/10* (2006.01)
  *G06T 7/33* (2017.01)
  *G06T 5/50* (2006.01)
  *G06T 5/00* (2006.01)
  *G06T 5/20* (2006.01)
  *G06T 11/00* (2006.01)

(52) U.S. Cl.
  CPC .................. *G06T 5/20* (2013.01); *G06T 5/50* (2013.01); *G06T 7/0012* (2013.01); *G06T 7/33* (2017.01); *G06T 11/008* (2013.01); *A61B 6/4441* (2013.01); *A61N 2005/1061* (2013.01); *G06T 2207/10081* (2013.01); *G06T 2207/30004* (2013.01); *G06T 2211/421* (2013.01)

(56) References Cited

U.S. PATENT DOCUMENTS

| | | | |
|---|---|---|---|
| 2010/0172556 A1* | 7/2010 | Cohen | A61B 5/4836 382/128 |
| 2010/0183118 A1* | 7/2010 | Star-Lack | A61B 6/5205 378/23 |
| 2011/0116703 A1 | 5/2011 | Fu et al. | |
| 2011/0176723 A1 | 7/2011 | Ali et al. | |
| 2013/0034286 A1 | 2/2013 | Vija et al. | |
| 2013/0108136 A1 | 5/2013 | Sebok | |
| 2013/0259338 A1* | 10/2013 | Brehm | G06T 11/008 382/131 |
| 2014/0270440 A1* | 9/2014 | Inglese | A61B 6/5205 382/131 |
| 2015/0356728 A1 | 12/2015 | Nakanishi et al. | |

\* cited by examiner

AUTOMATED TRACKING OF FIDUCIAL MARKER CLUSTERS IN X-RAY IMAGES

CROSS-REFERENCE TO RELATED APPLICATIONS

This application claims priority to U.S. Provisional Application Ser. No. 62/368,870 filed Jul. 29, 2016, which is incorporated herein by reference in its entirety for all purposes.

TECHNICAL FIELD

Various embodiments of the present technology generally relate to identification of tumor location. More specifically, some embodiments of the present technology relate automated tracking of fiducial marker clusters in x-ray images for the real-time identification of tumor location and guidance of radiation therapy beams.

BACKGROUND

Tumors are often difficult to identify in photon-based imaging due to similarities between normal and tumor tissue. A common approach to improve target visibility is to implant radio-opaque fiducial markers in, or near, the tumor. These dense, metal objects serve as easy-to-find landmarks of the tumor position in planar kV/MV imaging, or in cone-beam computed tomography (CBCT). In radiation therapy, a physician will examine these markers in a CBCT scan acquired just prior to treatment in order to localize the tumor with the isocenter of the treatment beam.

In some instances, intra-fractional monitoring of these markers can also allow for positional verification of the target during treatment, often to accommodate respiratory gating. Furthermore, offline review of CBCT scans can provide valuable data on the motion of fiducial markers, which can inform choices related to margin selection and motion management. The latter two cases call for automated techniques rather than manual techniques, due to a need for quick reaction time and due to the high workload involved, respectively.

Many traditional methods techniques for locating radio-opaque markers in x-ray images are based on template matching. Simply, template matching attempts to find an object in a sample image using a template image that is representative of that object. A 2D normalized cross-correlation of the template image with a sample image provides a pixel map of cross-correlation scores ranging between $-1$ and $1$. A pixel with a score of 1 indicates that the exact object was located at that pixel's location, and a score of $-1$ indicates that an exact inverse of the object was found (i.e., a 'negative' image of the object). Essentially, template matching identifies high-contrast regions of an image whose shape resembles that of the template. When detecting fiducial markers used for radiation therapy, the process can be obscured by other high-contrast features of the image, such as bony anatomy, air pockets, or other metallic objects. In practice, marker templates are typically based on the properties of a single marker.

Templates can be prepared for spherical and cylindrical markers by using their known dimensions and the geometry of the imaging setup. For cylindrical markers, imaging can help to indicate their position and orientation, allowing for templates to be prepared according to imaging angle. Some markers call for images to be acquired due to arbitrarily shaped markers or due to deformation that can occur during implantation (e.g., coil markers). These so called 'coaching' images can be used to produce templates for subsequent tracking. However, a cyclical challenge presents itself whenever such coaching images need to be used for a template production technique that is meant to be fully automated. That is, how does one reliably and in a fully automated manner detect markers in coaching images in order to create templates that will later be used to reliably and in a fully automated manner detect the same markers in clinical images?

As such, there are a number of challenges and inefficiencies created in traditional automation of the fiducial markers detection in clinical images. For example, methods for template generation have either required some form of manual selection by the user, or required that assumptions be made about the shape of markers. Thus, it can be difficult to reliably detect the markers in a fully automated manner. It is with respect to these and other problems that embodiments of the present invention have been made.

SUMMARY

Systems and methods are described for automated tracking of fiducial marker clusters in x-ray images for the real-time identification of tumor location and guidance of radiation therapy beams. More specifically, some embodiments provide for automated method for producing high quality, dynamic templates of fiducial marker clusters from a single imaging scan (e.g., CBCT scan). These techniques can provide motion tracking data for planar imaging. Some embodiments can crop templates when portions of the cluster fell outside of the imager's field-of-view. Some embodiments can use static and/or dynamic templates.

Various embodiments provide for a method that includes receiving multiple projection images collected using a cone beam computed tomography (CBCT) scan of a patient having a cluster of fiducial markers. Filtered marker enhanced images can be generated from the multiple projection images using one or more filters. Then a three-dimensional volume reconstruction can be generated by applying a filtered back projection on the filtered marker enhanced images. To produce final stabilized filtered marker images, some embodiments can repeat the following steps multiple times: 1) apply a forward projection to the three-dimensional volume reconstruction to create a set of static image templates; 2) stabilize, using gating information collected during the CBCT scan and the set of static image templates, the filtered marker enhanced images to produce stabilized filtered marker enhanced images; and 3) apply an additional filtered back projection to the stabilized filtered marker enhanced images to update the three-dimensional volume reconstruction.

Some embodiments can use processed CBCT projection images as part of an automated routine of reconstruction, forward-projection, tracking, and stabilization generated static templates of the marker cluster at arbitrary viewing angles. Breathing data can then be incorporated into the same routine, resulting in dynamic templates dependent on both viewing angle and breathing motion. In some embodiments, marker clusters can be tracked using normalized cross correlations between templates (either static or dynamic) and CBCT projection images.

Embodiments of the present invention also include computer-readable storage media containing sets of instructions to cause one or more processors to perform the methods, variations of the methods, and other operations described herein.

By tracking clusters of fiducial markers, some embodiments can perform automated tracking accurately despite the presence of radio-opaque, nonmarker objects (e.g., metallic stents, surgical clips). Dynamic templates can be used by some embodiments to produce higher cross-correlation scores than static templates in patients whose fiducial marker clusters exhibit considerable deformation or rotation during the breathing cycle.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the scope of the present invention. Accordingly, the drawings and detailed description are to be regarded as illustrative in nature and not restrictive.

BRIEF DESCRIPTION OF THE DRAWINGS

Embodiments of the present technology will be described and explained through the use of the accompanying drawings in which.

Figure 1:
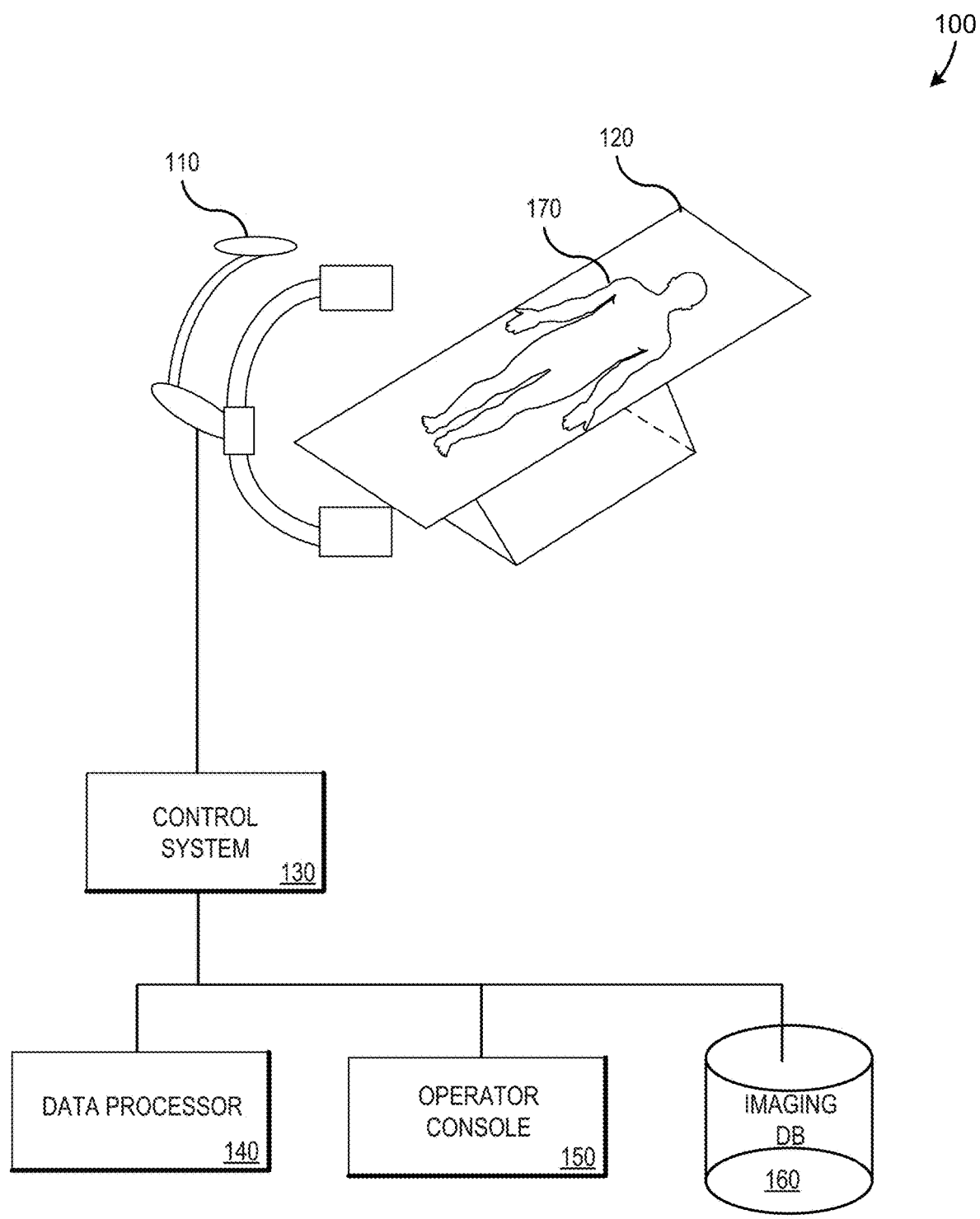
FIG. 1 illustrates an example of an imaging system which can be used in some embodiments of the present technology.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

Various embodiments of the present technology generally relate to identification of tumor location. More specifically, some embodiments of the present technology relate automated tracking of fiducial marker clusters in x-ray images for the real-time identification of tumor location and guidance of radiation therapy beams. Implanted fiducial markers are often used in radiotherapy to facilitate accurate visualization and localization of tumors. Typically, such markers are used to aid daily patient positioning and to verify the target's position during treatment. These markers can also provide a wealth of information regarding tumor motion, yet determining their accurate position in thousands of images is often prohibitive. Various embodiments of the present technology introduce a novel, automated method for identifying fiducial markers in planar x-ray imaging.

Various embodiments of the present technology include template image generation that can use a single CBCT scan. Some embodiments provide for a fully automated approach (i.e., that requires no input from the user) and makes no assumptions about the shapes of markers. Instead of searching for fiducial markers individually, various embodiments treat the cluster of markers as a single entity, seeking out the cluster as a whole. The entire cluster is less likely than individual markers to be confused with other aspects of a patient's anatomy. Also, searching for the cluster as a whole, or group, eliminates the challenge of needing to differentiate individual markers when the individual markers overlap with one another. Some embodiments may construct templates from a prior CBCT scans and apply these templates to future treatments.

Some embodiments filter CBCT projection images to enhance the appearance of markers. Then, templates can be created from these filtered images through an iterative process that uses back-projection to reconstruct the cluster, and forward-projection in conjunction with image stabilization to adjust for motion and update the template. Once this loop converges on a static template, breathing data can be incorporated into the same process to construct 4D dynamic templates.

In order to strengthen the appearance of fiducial markers in projection images, some filtering can be performed. In some embodiments, a median-filtered version of each projection image can be subtracted from its unfiltered version. In the resulting marker-enhanced (ME) image, values less than zero may be set equal to zero, leaving behind the highly radio-opaque markers, some edge features (e.g., from vertebrae and gas in the bowels), and some random noise. Once ME images are calculated for all projections in a CBCT scan, ME images can be additionally filtered in sinogram space in all three directions (e.g., using a linear Savitzky-Golay filter). Then, the histories of individual pixels can be examined, and for any projections during the scan where a pixel's value fell below a threshold (e.g., its 60th percentile value), its value for that projection was set equal to zero. Finally, each projection image may be filtered again using a median filter and then an adaptive noise-removal filter. These filtered marker-enhanced (FME) images can be used for template production and motion tracking.

After projection images have been filtered, some embodiments produce a crude reconstruction of the fiducial marker cluster by using filtered back-projection with FME images using a fan-beam geometry. In the resulting crude reconstruction, voxels with values below a threshold (e.g., 70% of the maximum value) can be set equal to zero, Gaussian filtering can be used to clean up the resulting volume, and the 3D centroid of the cluster can be aligned at the center. Then, using forward-projection, template images can be calculated as a function of gantry angle. Using this set of template images, the cluster can then be tracked throughout the scan using normalized cross-correlations of template images and FME images. An initial tracking of the maximum cross-correlation score can be used to determine the longest consecutive chain of positions (i.e., without large displacements between frames). From the midpoint in this chain, forward tracking and backward tracking can be performed by considering only local maxima using a window centered on the previously tracked position.

Some embodiments can use a local window that helps to reduce computing time and prevent large erroneous shifts to short-lived distant maxima. Once cluster positions are tracked throughout the scan, FME images can be stabilized based on these positions by centering the cluster in frame. Using this stabilized data, a reconstruction that is more representative of the fiducial marker cluster could be produced. By repeating this loop of (i) tracking & stabilizing FME images, (ii) reconstructing stabilized data, and (iii) forward-projecting template images, a set of high quality static templates—images as a function of gantry angle—passing ranges. After this loop is completed (e.g., after a fixed number of iterations or based on some decision criteria) a second loop can be performed to create a set of high quality dynamic templates—images as a function of gantry angle and breathing amplitude, respectively.

It should be noted that, although marker tracking can be used in various embodiments of the template production, marker tracking can still be performed independently from template production. For example, templates can be prepared in advance offline using data from a prior scan. This can create a reduction in computational resources and may be often combine with real-time tracking in some embodiments. Motion tracking, which can be used for template production, is discussed in more detail below.

Some embodiments of the present technology use respiratory gating information (e.g., breathing data acquired by cameras on the treatment unit, optical surface monitoring, or other devices) to aid in the reconstruction of 4D volumes. Some embodiments can use the tracked positions obtained in the first iterative loop to reconstruct 4D volumes. For example, in the absence of gating information. As a result, dynamic templates can be created in some embodiments without breathing data being provided. Instead, the breathing data is essentially obtained when the position of the cluster is tracked.

In addition, some embodiments of the present technology use projection images from cone beam CT. However, systems and techniques can be used for generating the projection images and can be applied using any set of x-ray images acquired with an orbital source trajectory. Other systems that can be used include, but are not limited to, C-arm CT or certain types of fluoroscopy.

Various embodiments provide a fully automated workflow for simultaneously achieving two goals: (1) creating high-quality templates of fiducial marker clusters, and (2) accurately identifying fiducial marker clusters in planar images. Although marker tracking and template production are coupled in some embodiments, marker tracking can still be performed later, independent from template production. Computationally intensive parts of the routine can be executed in advance by preparing templates beforehand using data from a prior scan. Because of this structure, highly accurate real-time tracking could be accomplished with only a relatively inexpensive cross-correlation calculation.

Templates produced using various embodiments have the potential to be particularly useful for intrafractional monitoring during arc therapy techniques. One common approach to real-time 3D tracking of markers is to use orthogonal kV/MV images acquired during treatment. With unique templates being produced for all gantry angles, orthogonally tracked 2D positions would be able to pinpoint the target in 3D. Some embodiments use a cropping technique to maintain tracking in many instances where only a portion of the cluster was visible by the imager. Such a technique may also be used for target tracking in portal images of beams that are slightly off target or have been modulated by a multi-leaf collimator.

In the following description, for the purposes of explanation, numerous specific details are set forth in order to provide a thorough understanding of embodiments of the present technology. It will be apparent, however, to one skilled in the art that embodiments of the present technology may be practiced without some of these specific details.

The techniques introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions which may be used to program a computer (or other electronic devices) to perform a process. The machine-readable medium may include, but is not limited to, floppy diskettes, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions.

Terminology

Brief definitions of terms, abbreviations, and phrases used throughout this application are given below.

The terms "connected" or "coupled" and related terms are used in an operational sense and are not necessarily limited to a direct physical connection or coupling. Thus, for example, two devices may be coupled directly, or via one or more intermediary media or devices. As another example, devices may be coupled in such a way that information can be passed therebetween, while not sharing any physical connection with one another. Based on the disclosure provided herein, one of ordinary skill in the art will appreciate a variety of ways in which connection or coupling exists in accordance with the aforementioned definition.

The phrases "in some embodiments," "according to some embodiments," "in the embodiments shown," "in other embodiments," and the like generally mean the particular feature, structure, or characteristic following the phrase is included in at least one implementation of the present invention, and may be included in more than one implementation. In addition, such phrases do not necessarily refer to the same embodiments or different embodiments.

If the specification states a component or feature "may", "can", "could", or "might" be included or have a characteristic, that particular component or feature is not required to be included or have the characteristic.

The term "module" refers broadly to a software, hardware, or firmware (or any combination thereof) component. Modules are typically functional components that can generate useful data or other output using specified input(s). A module may or may not be self-contained. An application program (also called an "application") may include one or more modules, or a module can include one or more application programs.

GENERAL DESCRIPTION

FIG. 1 illustrates an example of an imaging system 100 which can be used in some embodiments of the present technology. In the embodiments illustrated in FIG. 1, imaging system 100 may include imaging device 110, bed 120, control system 130, data processor 140, operator console 150, and imaging database 160. Once patient 170 is positioned and secured on bed 120, an operator can use operator console 150 to command the bed to move the patient to a desired location before activating imaging device 110. The desired scanning sequences can then be initiated to generate images of various body parts (e.g., heart, brain, lungs, wrists, knees, ankles, cartilage, etc.) of patient 170. The set of images can be displayed on a fluorescent screen or monitor associated with operator console 150.

An operator can use operator console 150 to select and control the scans as well as review results. As the scan is selected by the operator, control system 130 controls imaging device 110 to scan patient 170. As the results from the scans are received, data processor 140 can process the data to generate one or more images that can be displayed via operator console 150. For example, data processor 140 may include one or more modules to transform a set of images into a motion model that can be displayed in operator console 150. The data returned from imaging device 110 and/or images created by data processor 140 can be stored in database 160.

In accordance with various embodiments, patient 170 may have multiple fiducial markers (e.g., cylindrical or coil markers) implanted to help visualize the target volume and accentuate tumors that suffer from poor contrast. When imaging device 110 scans the patient, the resulting images of these markers allows for verification of target position and target motion prior to treatment of patient 170. However, these highly radio-opaque objects can cause considerable artifacts in CT reconstructions, which can decrease soft-tissue contrast and obscure nearby low-contrast structures. Data processor 140 can include an automated method of segmenting arbitrarily-shaped fiducial markers in projection data prior to reconstruction. For example, in some embodiments, data processor 140 can subtract median filtered data respectively from unfiltered data, thereby enhancing outliers (e.g., small, dense markers). Using enhanced-outlier data, masks can then be calculated to denote regions for replacement in unfiltered data, and a repeated subtraction of region-replaced data from the original data provides images with highly enhanced markers.

Some embodiments of the present technology provide a novel method of template image generation that can use a single CBCT scan. Various embodiments can be fully automated, require no input from the user, and make no assumptions about the shapes of markers. Instead of searching for fiducial markers individually, some embodiments treat the cluster of markers as a single entity, seeking out the cluster as a whole. The entire cluster is less likely than individual markers to be confused with other aspects of a patient's anatomy. Also, searching for the cluster as a whole eliminates the challenge of needing to differentiate individual markers within patient 170 when individual markers overlap with one another.

Control system 130 may be used in one or more embodiments of the present technology. Control system 130 can include a communication interface for communicating with imaging device 110 and operator console 150. In accordance with various embodiments, control system 140 can receive operator commands from operator console 150, process those requests, and issue commands to imaging device 110 indicating the scan sequence. Control system 130 may also include a physiological acquisition controller that can receive signals from different sensors to identify gating or other physiological data. This information can detect additional patient information (e.g., movement, heart rate, respiratory patterns, etc.) which can be used in creating enhanced images by data processor 140.

Figure 2:
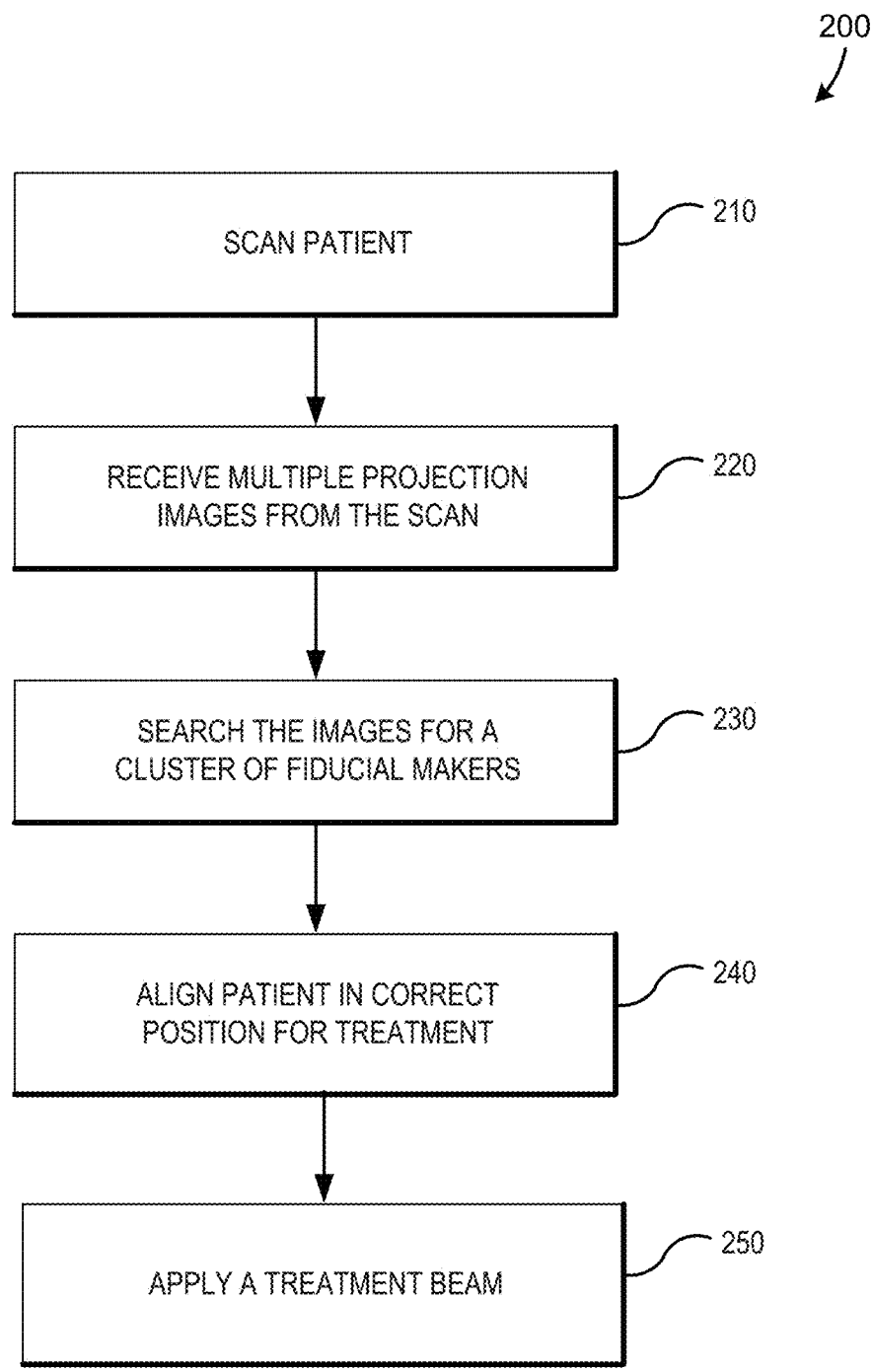
FIG. 2 illustrates an example of a set of operations for identifying a location to apply a treatment beam that may be used in one or more embodiments of the present technology.

FIG. 2 illustrates an example of a set of operations 200 for identifying a location to apply a treatment beam that may be used in one or more embodiments of the present technology. As illustrated in FIG. 2, scanning operation 210 scans the patient and generates multiple images. The images may be stored in a database (e.g., imaging database 160 illustrated in FIG. 1 or directly transmitted to a data processor). Once these images are received during receiving operation 220, the system can initiate searching operation 230, where the images are evaluated and processed to identify a cluster of fiducial markers. Searching operation 230 may include the use of various static and/or dynamic templates, volume reconstruction, and/or other techniques described in more detail below. Once the cluster of fiducial markers has been located by searching operation 230, alignment operation 240 can align the patient and/or equipment in a correct position for treatment. During application operation 240 a treatment beam can be applied.

Figure 3:
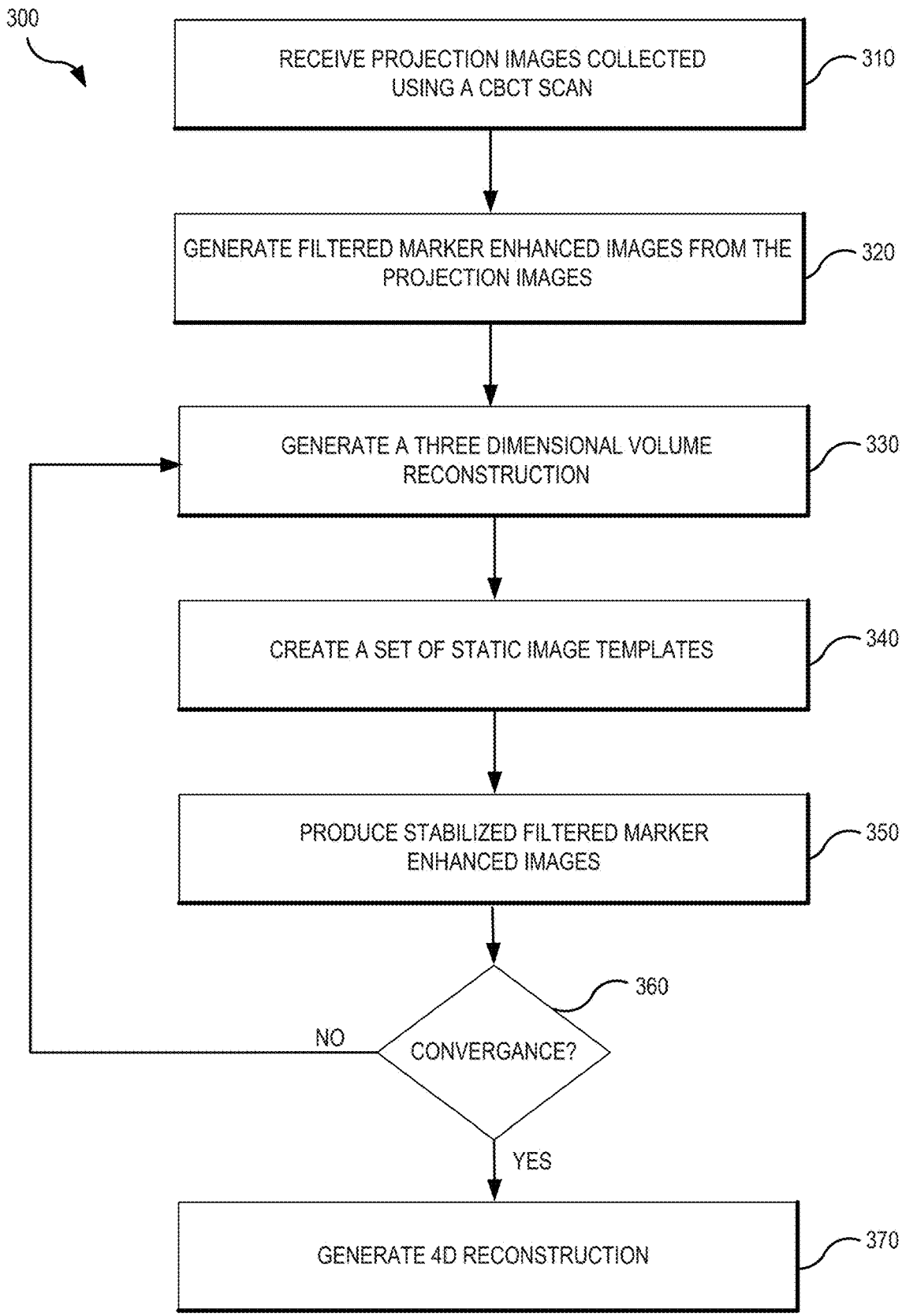
FIG. 3 illustrates an example of a set of operations that may be used to generate a 4D reconstruction of a set of images according to one or more embodiments of the present technology.

FIG. 3 illustrates an example of a set of operations 300 that may be used to generate a 4D reconstruction of a set of images according to one or more embodiments of the present technology. As illustrated in FIG. 3, receiving operation 310 receives a set of medical images (e.g., from a database, scanning device, real-time data feed, or other location). As the images are received, filtering operation 320 can generate a filtered marker enhanced set of images from the images received via receiving operation 310. In accordance with various embodiments different filters may be used. For example, during filtering operation 320 some embodiments may apply a polynomial filter, an adaptive mean filter, and/or some other type of filter to enhance the set of images so that the markers are more easily identified.

Filtering operation 320 can strengthen the appearance of fiducial markers in projection images. In some embodiments, a median-filtered version of each projection image can be subtracted from its unfiltered version. In the resulting marker-enhanced (ME) image, values less than zero may be set equal to zero, leaving behind the highly radio-opaque markers, some edge features (e.g., from vertebrae and gas in the bowels), and some random noise. Once ME images are calculated for all projections in a CBCT scan, ME images can be additionally filtered in sinogram space in all three directions (e.g., using a linear Savitzky-Golay filter). Then, the histories of individual pixels can be examined, and for any projections during the scan where a pixel's value fell below a threshold (e.g., 60th percentile value), the pixel value for that projection can be set equal to zero. Finally, each projection image may be filtered again using a median filter and then an adaptive noise-removal filter. These filtered marker-enhanced (FME) images can be used for template production and motion tracking.

During reconstruction operation 330, a three-dimensional volume reconstruction can be created. For example, in some embodiments, reconstruction operation 330 can use FME projection images and corresponding angles that each projection image was acquired from to create the three-dimensional volume reconstructions. Some embodiments use filtered back-projection using fan-beam geometry (even if the actual geometry of the beam is a cone-beam). In some embodiments, reconstruction operation 330 can apply an inverse Radon transform to generate a three-dimensional reconstruction of the fiducial marker position using the filtered two-dimensional data as input.

After projection images have been filtered by filtering operation 320, some embodiments produce a crude reconstruction of the fiducial marker cluster by using filtered back-projection with FME images using a fan-beam geometry. Other reconstruction techniques could be applied, such as the Feldkamp-Davies-Kress (FDK) reconstruction algorithms, or iterative reconstruction techniques. In the resulting crude reconstruction, voxels with values below a threshold (e.g., 70% of the maximum value) can be set equal to zero, Gaussian filtering can be used to clean up the resulting volume, and the 3D centroid of the cluster can be aligned at the center. These operations can help to eliminate other portions of the two-dimensional images that do not represent fiducial markers, and help allow the technique to focus only on the signal of the fiducial markers.

In addition, template creation operation 340 can create a set of static image templates. Using forward-projection, template images can be calculated as a function of gantry angle using forward-projection on the 3D volume reconstructed in reconstruction operation 330. Then, using the set of static image templates, a set of stabilized filtered marker enhanced images can be produced during stabilization operation 350. In stabilization operation 350, FME images are stabilized by first tracking the position of the cluster throughout the scan using normalized cross-correlations of template images and FME images, and then centering the cluster in each image. This removes the effect of motion from the process and allows for sharper templates of the markers to be constructed. To aid in automation, an initial tracking of the maximum cross-correlation score can be used to determine the longest consecutive chain of positions (i.e., without large displacements between frames). From the midpoint in this chain, forward tracking and backward tracking can be performed by considering only local maxima using a window centered on the previously tracked position.

Determination operation 360 can determine whether the stabilized filtered marker enhanced images have converged. Determination operation 360 may have a variety of criteria for determining when to stop the iterations. For example, various embodiments may track an iteration number. When the iteration number reaches a pre-specified number of iterations (e.g., 3, 5, 10, etc.) the loop may exit. This technique may be applied with or without other convergence criteria. Some embodiments may monitor normalized cross-correlation scores. When determination operation 360 determines that these scores no longer increase (or increase very little). As another example, determination operation 360, in some embodiments, can track cluster motion and when the cluster motion no longer changes with additional iterations a determination over convergence may be made. These criteria and other criteria for determining convergence can be combined in some embodiments. For example, if no projection score shows an increase greater than one percent or no projections show a position changes greater than 0.5 mm, then determination operation may indicate that the marker enhanced images have converged. When determination operation 360 determines that the stabilized filtered images have not converged, then determination operation 360 branches to reconstruction operation 330 where the current set of stabilized filtered marker enhanced images are used to create the three-dimensional reconstruction.

When determination operation 360 determines that the stabilized filtered images have converged, then determination operation 360 branches to 4D reconstruction operation 370 where a 4D model is created. For most patients, the quality of images returned from reconstruction operation 370 will be sufficient to identify the markers and treatment area. However, in some cases, additional processing may be needed which is described in more detail in FIG. 4. This additional processing may be manually selected via operator console (e.g., 150 in FIG. 1) or may be automatically selected when various processing criteria is met.

Figure 4:
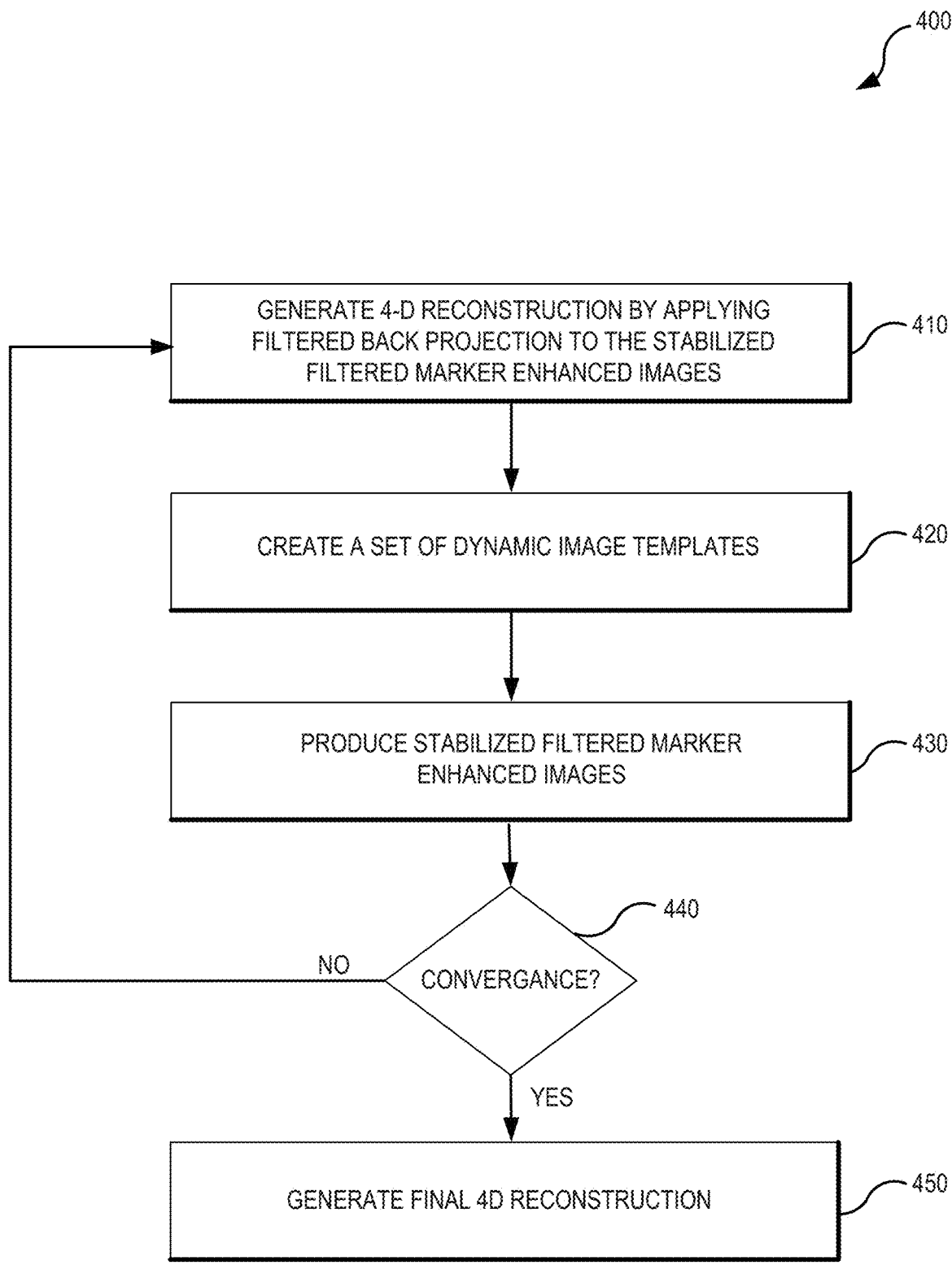
FIG. 4 illustrates an example of a set of operations that may be used to produce a 4D reconstruction of a set of images according to one or more embodiments of the present technology.

FIG. 4 illustrates an example of a set of operations 400 that may be used to produce a 4D reconstruction of a set of images according to one or more embodiments of the present technology. The fourth dimension represents a temporal component to the template, meaning that the template changes over the respiratory cycle of the subject. As illustrated in FIG. 4, generation operation 410 can generate a 4D reconstruction by applying filtered back-projection (or other reconstruction technique) to the stabilized FME images binned, either according to breathing data acquired during the scan or by cluster positions tracked during stabilization operations 350/430. Template operation 420 can create a set of dynamic image templates from the 4D reconstruction using forward-projection in a manner similar to 340.

These templates can then be used by stabilization operation 430 to produced stabilized filtered marker enhanced images by first tracking the position of the cluster throughout the scan using normalized cross-correlations of template images and FME images, and then centering the cluster in each image. In accordance with one or more embodiments, stabilization operation 430 may be similar to stabilization operation 350. When determination operation 440 determines that these stabilized filtered marker enhanced images have converged, then determination operation 440 branches to 4D reconstruction operation 450 which generates a final 4D reconstruction based on the most recent set of stabilized FME images and binning data (i.e., breathing data or tracked cluster positions). When determination operation 440 determines that these stabilized filtered marker enhanced images have not converged, then determination operation 440 branches to generation operation 410.

Figure 5:
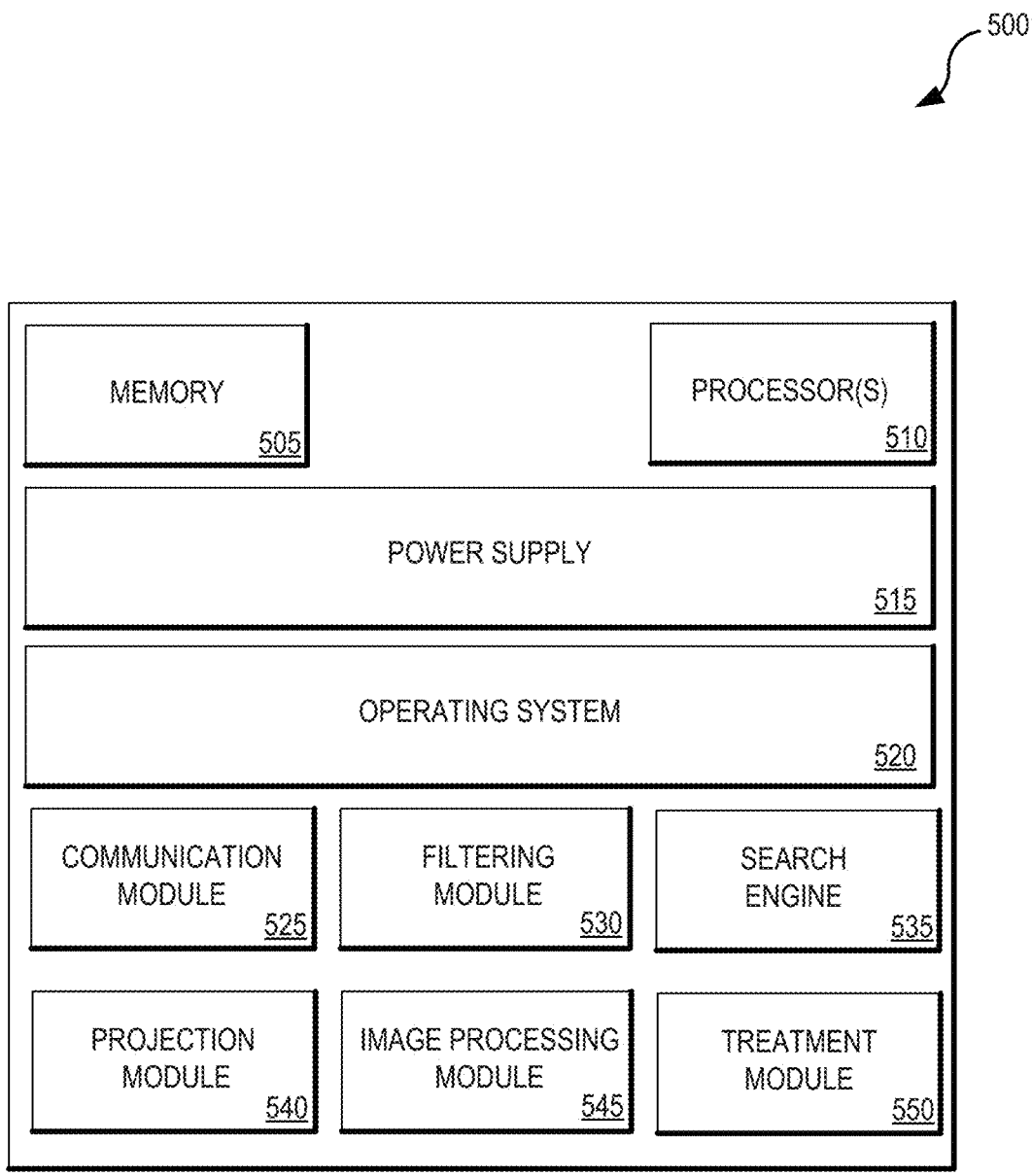
FIG. 5 illustrates a set of components that may be used in a data processor in accordance with some embodiments of the present technology.

FIG. 5 illustrates a set of components 500 that may be used in a data processor 140 in accordance with some embodiments of the present technology. As illustrated in FIG. 5, data processor 140 can include memory 505 (e.g., volatile memory and/or nonvolatile memory), processor(s) 510 for executing processing instructions, power supply 515, operating system 520, communication module 525, filtering module 530, search engine 535, projection module 540, image processing module 545, and treatment module 550. Each of these modules can be embodied as special-purpose hardware (e.g., one or more ASICS, PLDs, FPGAs, or the like), or as programmable circuitry (e.g., one or more microprocessors, microcontrollers, or the like) appropriately programmed with software and/or firmware, or as a combination of special purpose hardware and programmable circuitry. Other embodiments of the present technology may include some, all, or none of these modules and components along with other modules, applications, and/or components. Still yet, some embodiments may incorporate two or more of these modules and components into a single module and/or associate a portion of the functionality of one or more of these modules with a different module. For example, in one embodiment, filtering module 530 and search engine 535 can be combined into a single module for processing data from an imaging device.

Memory 505 can be any device, mechanism, or populated data structure used for storing information. In accordance with some embodiments of the present technology, memory 505 can encompass any type of, but is not limited to, volatile memory, nonvolatile memory and dynamic memory. For example, memory 505 can be random access memory, memory storage devices, optical memory devices, media magnetic media, floppy disks, magnetic tapes, hard drives, SDRAM, RDRAM, DDR RAM, erasable programmable read-only memories (EPROMs), electrically erasable programmable read-only memories (EEPROMs), compact disks, DVDs, and/or the like. In accordance with some embodiments, memory 505 may include one or more disk drives, flash drives, one or more databases, one or more tables, one or more files, local cache memories, processor cache memories, relational databases, flat databases, and/or the like. In addition, those of ordinary skill in the art will appreciate many additional devices and techniques for storing information which can be used as memory 505.

Memory 505 may be used to store instructions for running one or more applications or modules on processor(s) 510. For example, memory 505 could be used in one or more embodiments to house all or some of the instructions needed to execute the functionality of operating system 520, communication module 525, filtering module 530, search engine 535, projection module 540, image processing module 545, and treatment module 550. Operating system 520 can provide a software package that is capable of managing various hardware resources of data processor 140.

Communication module 525 can be used to receive and transmit various communications between components of an imaging system. For example, communication module 525 can receive commands from an operator console or retrieve information or images from various databases or cloud-services. In some embodiments, data processor 140 can use communication module 525 to receive multiple projection images of a patient having a cluster of fiducial markers. Filtering module 530 can be configured to generate filtered marker enhanced images from the multiple projection images using one or more filters. In some embodiments, filtering module 530 can generate a three-dimensional volume reconstruction by applying a filtered back projection on the filtered marker enhanced images created using projection module 540. In addition, filtering module can also apply a forward projection to the three-dimensional volume reconstruction to create a set of static image templates.

Search engine 535 can search the multiple projection images for the cluster of fiducial markers within a patient. In some embodiments, search engine 535 can search for the cluster of fiducial markers by generating a set of templates isolating the cluster of fiducial markers. Search engine 535 can also compensate for movement of the patient based on gating information collected during collection of the multiple projection images. Image processing module 545 can be configured to stabilize, using the set of static image templates, the filtered marker enhanced images to produce stabilized filtered marker enhanced images. Treatment module 550 can apply, upon identification of the cluster of fiducial markers, a treatment beam.

Phantom Data

Scans of a heterogeneous thorax phantom were acquired to evaluate the accuracy of various embodiments of the template tracking technique. Four fiducial markers (e.g., gold, cylindrical, 5 mm length, 1 mm diameter) were positioned inside of the phantom, and movement of the phantom was performed using three orthogonal, linear robotic stages. Three scans of the phantom were acquired: one where no motion was imposed (0D), one where motion was imposed only in the superior-inferior direction (1D), and one where motion was imposed in all three directions (3D). The magnitude of motion imposed on the phantom was chosen to be representative of typical motion observed in the pancreatic cancer patients also evaluated in this work (left-right, anterior-posterior, and superior-inferior ranges of motion of 5 mm, 5 mm, and 10 mm, respectively).

Patient Data

Seventy-five CBCT scans were acquired of 15 patients receiving stereotactic body radiation therapy for pancreatic cancer. These were routine patient alignment scans taken just prior to the delivery of each of their five treatment fractions. Prior to simulation and treatment planning, each patient had 3-4 fiducial markers (e.g., titanium-coated carbon, roughly cylindrical, 5 mm length, 1 mm diameter) implanted in their tumor in order to aid daily 3D target localization. For the purposes of motion mitigation, abdominal compression was used for all 15 patients. To allow for the collection of breathing data during each scan, an infrared reflector external marker block was positioned on the patient's upper abdomen, roughly midway between the superior edge of the compression belt and the patient's xiphoid process, and a camera was used to track the respiration.

Template Production

Figure 6:
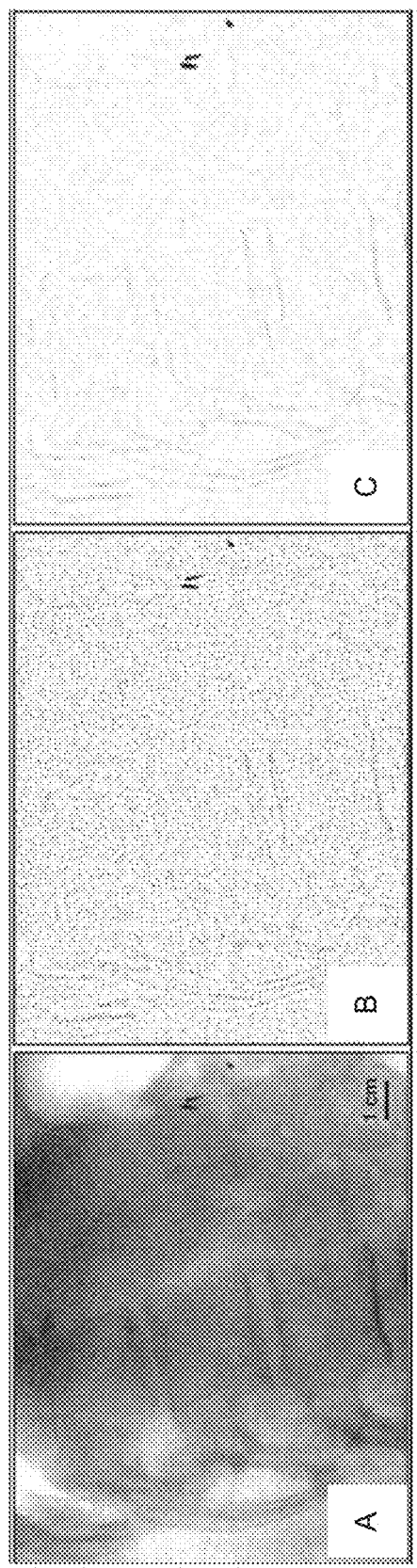
FIGS. 6A-6C illustrate a set of images that may be generated in accordance with one or more embodiments of the present technology.

Various embodiments of the present technology can first process CBCT projection images to enhance the appearance of markers (see FIG. 6). Then, a set of static templates (dependent on gantry angle) can be created from these processed images through an iterative routine that uses filtered back-projection to reconstruct the cluster, forward-projection to create template images, and template tracking to correct for motion seen in projection images. Once this loop converges on a set of static templates, breathing data can be incorporated into the same process to construct a set of 4D dynamic templates (dependent on both gantry angle and breathing motion).

FIGS. 6A-6C illustrate a set of images that may be generated in accordance with one or more embodiments of the present technology. Three fiducial markers can be seen in these examples from patient #8 of (a) a projection image, (b) a marker-enhanced image, and (c) a filtered marker-enhanced image. The scale indicator in (a) shows 1 cm as projected at the isocenter.

Figure 7:
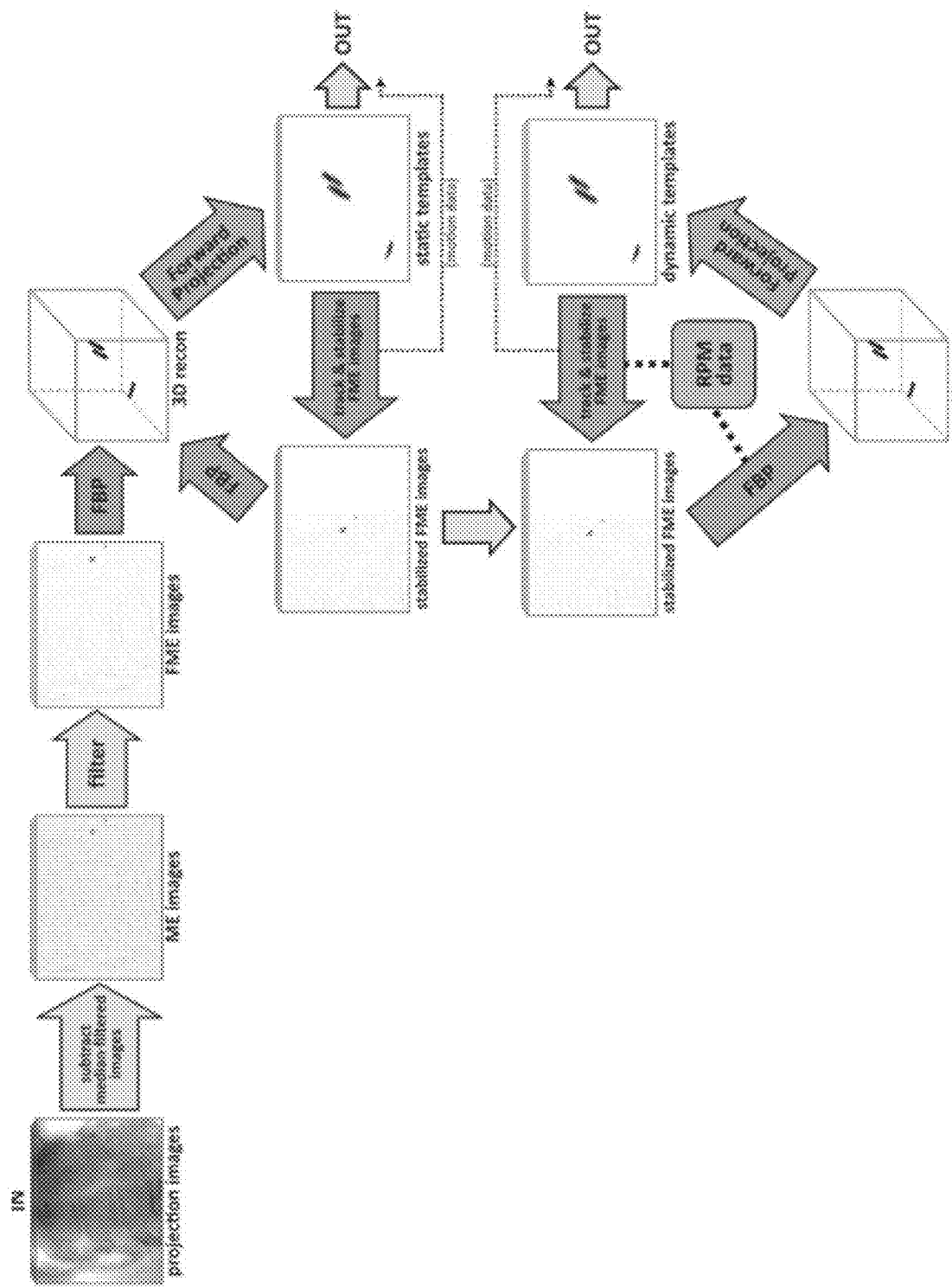
FIG. 7 illustrates a set of operations that may be used to produce static and dynamic templates in accordance with some embodiments of the present technology.
Figure 8:
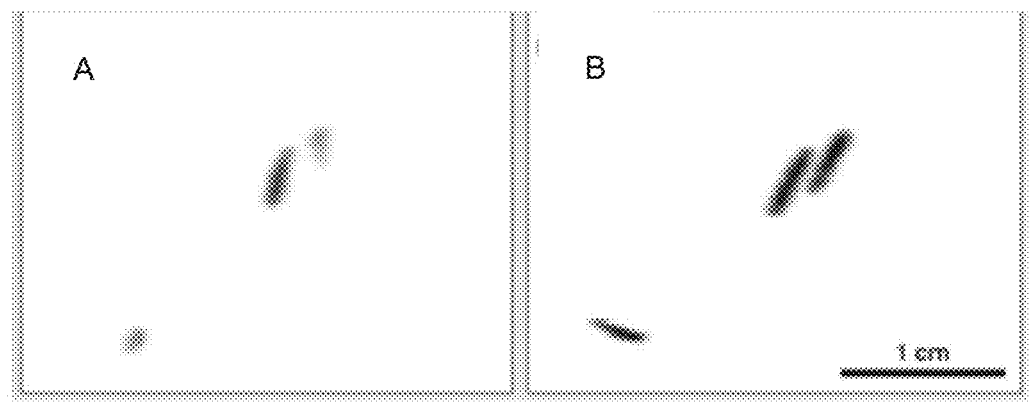
FIG. 8A illustrates an example of a template produced from an initial, crude reconstruction that may be produced according to various embodiments of the present technology.
FIG. 8B illustrates an example of a template produced after three iterations of the track and stabilize, reconstruct, and forward-project loop used in one or more embodiments of the present technology.
FIG. 8C illustrates a normalized cross-correlation of a template with an FME image that may be produced according to various embodiments of the present technology.
FIG. 8D illustrates a local window that may be identified in one or more embodiments of the present technology.
FIG. 8E illustrates a mask of FAHM pixels that may be selected in some embodiments of the present technology.
Figure 8:
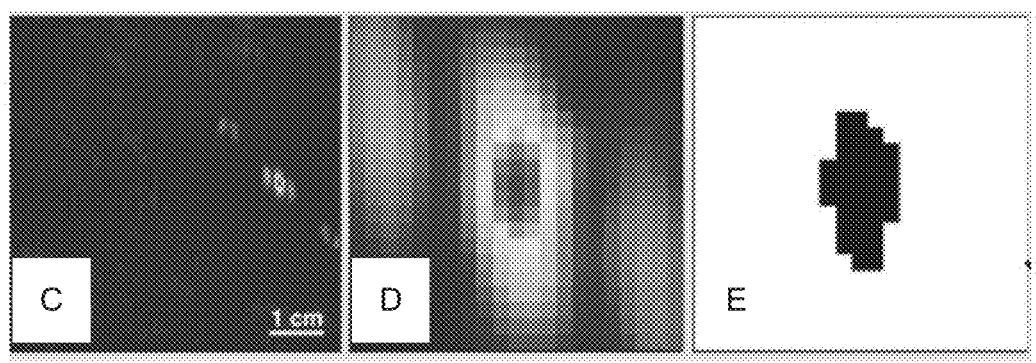

FIG. 7 illustrates a set of operations 700 that may be used to produce static and dynamic templates in accordance with some embodiments of the present technology as described below. FIG. 8A illustrates an example of a template produced from an initial, crude reconstruction that may be produced according to various embodiments of the present technology. More specifically, FIG. 8A illustrates an example of a template produced after three iterations of the track and stabilize, reconstruct, and forward-project loop used in one or more embodiments of the present technology. FIG. 8B illustrates a normalized cross-correlation of a template with an FME image that may be produced according to various embodiments of the present technology. FIG. 8D illustrates a local window that may be identified in one or more embodiments of the present technology. FIG. 8E illustrates a mask of FAHM pixels that may be selected in some embodiments of the present technology. More specifically, FIG. 8A example of a template produced from an initial, crude reconstruction, and FIG. 8B illustrates the template produced after three iterations of the track and stabilize, reconstruct, and forward-project loop. Using completed dynamic templates, examples from patient #8 are shown in FIG. 8C as normalized cross-correlation of a template with an FME image. The scale indicators in FIGS. 8B and 8C show 1 cm as projected at the isocenter, and both FIGS. 8D and 8E are square with sides equaling 5.43 mm.

To enhance the appearance of fiducial markers, which have an intensity value lower than surrounding pixels, CBCT projection images were processed in accordance with one or more embodiments using filtering methods in MATLAB. In the embodiments illustrated, median-filtered version of each projection image (e.g., using MATLAB command medfilt2, 9×9) was calculated. Then, these median-filtered images were subtracted from their respective originals, resulting in marker-enhanced (ME) images. In ME images, pixels with values greater than zero were set equal to zero, leaving behind the highly radio-opaque markers, some edge features (e.g., from bones and gas in the bowels), and some random noise. Next, ME images were then filtered in sinogram space in all three directions using a smoothing filter (e.g., using MATLAB command sgolayfilt, k=3, f=5). Other embodiments could use similar filters which reduce the effect of noise and enhance the appearance of the markers.

Then, the values of each individual pixel were examined across the entire scan, and for any projections during the scan when a pixel's value rose above its 40th percentile value, its value for that projection was set equal to zero. However, other embodiments may use different percentile values. This step is based on the assumption that markers are not likely to remain exactly at the isocenter, so markers should pass across any given pixel for only a portion of the scan (i.e., no more than 40% of the scan's duration). Finally, each projection image was filtered again using a median filter (e.g., using MATLAB command medfilt2, 3×3) and then an adaptive noise removal filter (e.g., using MATLAB command wiener2, 3×3). Other embodiments could use similar filters which reduce the effect of noise and enhance the appearance of the markers. The resultant filtered marker-enhanced (FME) images were used for template production and motion tracking. FIG. 6 shows examples of a projection image and its respective ME and FME images.

Filtered back-projection was used with FME images to provide a crude, initial reconstruction of the fiducial marker cluster. In the reconstructed volume, voxels with values below a threshold equal to 70% of the maximum value were set equal to zero and Gaussian filtering was used to clean up the resultant volume. The non-zero values that remained were assumed to represent the marker cluster, and these values were shifted so that their 3D center of mass aligned with the center of the volume. Then, forward-projection was used to produce 360 template images as a function of gantry angle (see FIG. 8A). Using this set of template images, the position of the cluster was tracked throughout the scan using normalized cross-correlations of template images and FME images (tracking is discussed in more detail in below). Once cluster positions were obtained, each FME image was stabilized by centering the cluster in frame. Using filtered back-projection with stabilized FME images, the volume that is reconstructed suffers from fewer motion artifacts and better resembles the fiducial marker cluster. By repeating this loop of (i) tracking and stabilizing FME images, (ii) reconstructing stabilized data, and (iii) forward-projecting template images, a set of high-quality static templates—360 images as a function of gantry angle—could be obtained (see FIG. 8B). Typically, high-quality templates were produced after three iterations. Some embodiments can loop until no significant increase in template matching cross correlation scores are observed.

After static templates were prepared, breathing data could be incorporated into the same iterative routine to produce dynamic templates that are a function of both gantry angle and respiratory motion. Using stabilized FME images, five different volumes were reconstructed for five different ranges of respiratory surrogate displacement. From each of these five volumes, a set of template images based on gantry angle were produced. In order to limit sudden changes in templates during tracking, the ranges (e.g., 5) of breathing amplitude used for reconstruction may be chosen to include overlap in various embodiments. Without overlapping ranges, a single template would be used for a given range of respiratory positions, and templates would suddenly change when the respiratory position transitioned from one range into another. Instead, with overlapping ranges, a weighted average of two overlapping templates was used. In this fashion, templates will not exhibit sudden changes when the position of the respiratory transitions between ranges.

Based on patient observations, which indicate longer dwell times in the end-exhalation phase, ranges for the five breathing amplitude bins were selected to include the Following percentiles: 0-40, 25-55, 40-70, 55-85, and 70-100, where 0 indicates end-Exhale and 100 indicates end-inhale. With the exception of values below 25 and above 85, templates selected during tracking were always a weighted-average of two templates, with weightings being dependent on the distance of the current respiratory position from the center of the two encompassing ranges. After the loop of (i) tracking and stabilizing, (ii) reconstructing stabilized data, and (iii) forward-projecting template images was repeated 2 or 3 times, a set of high-quality dynamic templates—360×5 images as a function of gantry angle and respiratory position, respectively—were produced.

Automated Tracking

Some embodiments employ various tracking techniques. In some embodiments, tracking with template matching can be used to determine the position of the target (i.e., the marker cluster) by locating the correct peak in the normalized cross-correlation of the projection image and the template. The correct peak, however, is not always the peak with the global maximum. Occasionally during a CBCT scan, image features that are not the true target (e.g., patient anatomy, foreign objects) can resemble the target, resulting in an erroneous peak. Almost always, these resemblances are short-lived, only bearing a similarity at certain angles. As such, some embodiments only search for peaks in a local window, reducing the likelihood of selecting an erroneous peak. This window can be chosen based on the expected position of the marker as predicted by a prior CT. Although, some fully automated tracking technique may not depend on this relatively old and possibly unreliable data.

Some embodiments may initially locate the global maximum in each cross-correlated image for the entire scan. Next, some embodiments may assume that the longest consecutive chain of global peak positions (i.e., without large displacements between frames) corresponded to the correct peak. Then, from the midpoint in this chain, forward tracking and backward tracking (i.e., towards the first and last images in the scan, respectively) can be performed by locating the local peak within a window centered on the previously tracked position. To allow for sub-pixel precision, in some embodiments, the position of each peak can be calculated as the center of mass of the 9 pixels within the local tracking window with the highest cross-correlation scores, regardless of whether or not these pixels were adjacent to one another.

FIG. 8C shows an example of a normalized cross-correlation (e.g., using MATLAB command normxcorr2) of a template with an FME image. For this work, a local window of 21×21 pixels (5.43×5.43 mm projected at the isocenter) was used for tracking (see FIG. 8D). Various factors can be used to inform the choice of dimensions of the resulting window. For example, some embodiments may use one or more of the following: (i) pixel dimensions, (ii) imaging frequency, and (iii) maximum expected speed of the target. For an accumulated set of 97 pancreatic cancer patients, the maximum instantaneous tumor speed observed was 3 cm/s. At this speed, with pixels being 0.259 mm projected at the isocenter and images being acquired every 0.0676 s, the position of a cluster to be displaced up to 8 pixels between frames. A 17×17 window would be capable of catching such displacements if only single pixel maxima were being used to localize the cluster. However, some embodiments may use a centroid of the 9 pixels with the highest values within the local window to calculate the cluster's position. Thus, in order to allow for the consideration of a cluster of 9 pixels, the local window may be expanded to fully encompass 2 pixels beyond the maximum displacement.

To reduce computing time, some embodiments may only consider a region-of-interest (ROI) (e.g., one quarter of the size of the imaging panel (384×512)). This ROI was centered about the isocenter in the superior-inferior direction. Due to the half-fan geometry of each scan, some ROI can be flush with the edge of the imager in the lateral direction so that as much of the patient near the isocenter could be observed. Cropping of the imaging panel in this manner in some embodiments may still allow for entire fiducial marker clusters to be fully visible for all scans, with the exception of incidences when clusters fall outside the field-of-view of the imaging panel due to the half-fan lateral shift.

Evaluation

In addition to automated tracking for all scans, and for the purpose of validating the automated method, users (e.g., 2 users) can manually track the positions of fiducial markers in the three phantom scans, and one user manually tracked markers for three scans from three patients. These measurements can be partly assisted by measurements obtained by the automated tracking technique, in that automatically tracked positions were used to show the user a zoomed-in region of each projection image, automatically magnifying the cluster. The MATLAB function ginput can be used to convert mouse clicks into sub-pixel measurements of the center of each marker, as judged by the user. One user repeated these measurements so that both interobserver and intraobserver precision could be evaluated.

In the phantom study, interobserver and intraobserver differences of manually determined marker positions were calculated for each marker in each projection image. Furthermore, the interobserver and intraobserver differences of the average position of multiple markers were calculated, up to and including all four markers. Due to the fact that the automated tracking technique seeks the entire cluster as a whole, it is only fair to compare automatically tracked positions against the averaged user-determined positions of all four markers. Known positions were calculated by smoothing the averaged measurements of all four markers and both users. In this way, sag of the imager was also accounted for. Errors in the phantom study were calculated as the magnitude of the 2D difference between the automatically tracked position and the known position. The criterion for successfully accurate tracking in the phantom study was an error <1 mm (projected at the isocenter).

For patient data, in addition to tracking the locations of marker clusters, three cross-correlation metrics were recorded during automated tracking to evaluate the strength of template matches. The first metric recorded during tracking was the maximum score of any single pixel within the local window, with scores closer to 1 indicating a better match. The second metric recorded was the global maximum score observed within the entire quarter-sized ROI area of the imaging panel. With this metric, the global tracking rate—the rate at which the local maximum was also the global maximum—can be monitored. Whenever the local maximum dropped below the global maximum, continuously tracking the cluster may be dependent on the use of a local search window. Finally, the third metric recorded was the number of pixels in the local window with values equal to or greater than half of the maximum value.

By multiplying these numbers by the area of a single pixel as projected at the isocenter, the full-area-half-max (FAHM) of the cross-correlation peak (see mask in FIG. 8E) can be effectively monitored. Akin to the full-width-halfmax for point spread and line spread functions, a smaller FAHM would denote a sharper peak, indicating a more precise match. Using manually tracked data from three patient scans, a relationship between FAHM and error magnitude can be established, where error magnitude was calculated as the difference between automatically tracked positions and manually selected positions. With this relationship, inferred absolute error values were calculated for all patient data in order to provide an indication of accuracy in real-life clinical scenarios where the ground truth is unknown. For patient data, the accuracy of tracked positions was verified by a visual check of stabilized scans, looking for any noticeable displacements during each scan.

Results—Phantom Study

Figure 9:
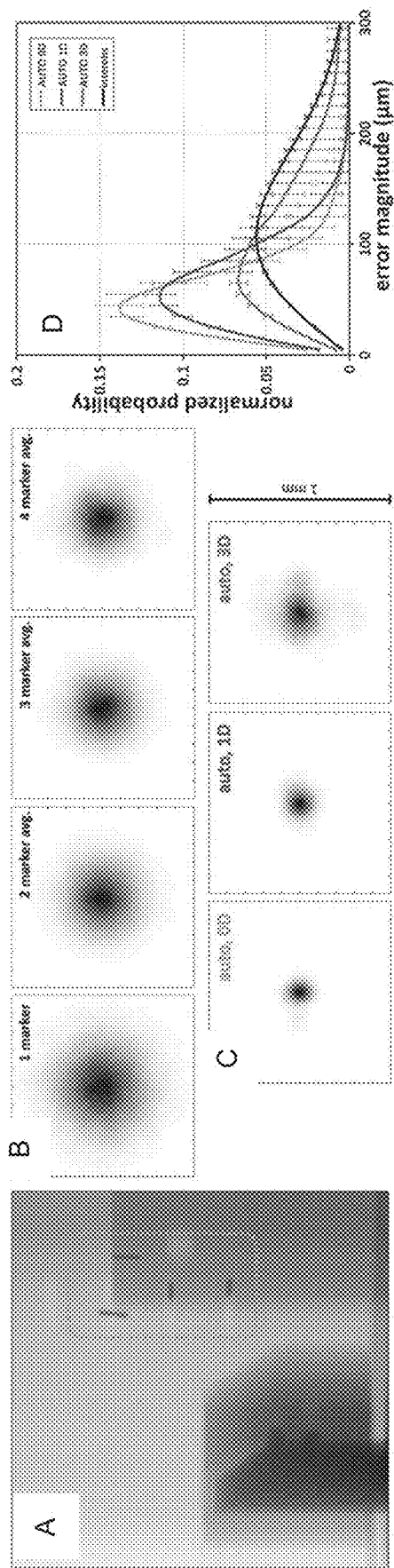
FIGS. 9A-9D illustrate results from a phantom study.

For all analysis in the phantom study, 2D differences and 2D errors were calculated relative to the coordinates of the imaging panel in units of micrometers as projected at the isocenter. FIG. 9A illustrates an example of a projection image with four markers indicated. FIG. 9B shows distributions of interobserver differences for single markers and for the averaged position of 2, 3, and 4 markers. The median magnitude of these differences were 183 µm, 145 µm, 129 µm, and 120 µm, respectively. For intraobserver differences, these values were 149 µm, 120 µm, 106 µm, and 98 µm, respectively.

Automated tracking in the phantom study was performed using static templates instead of dynamic templates due to the fact that no deformation or rotation of the marker cluster was possible in the experimental setup. FIG. 9C shows error distributions for the automated tracking technique in the 0D, 1D, and 3D phantom scans. Median error magnitudes for these scans were 39 µm, 53 µm, and 93 µm, respectively. Errors in all three scans were less than 1 mm (i.e., were successfully accurate) and had 99th percentiles of 152 µm, 174 µm, and 324 µm, respectively. Part of the increase in error magnitudes seen in the 1D and 3D scans was attributed to unavoidable vibrations of the phantom stage that occurred during motion. Normalized probability distributions for the automated tracking technique in the 0D, 1D, and 3D scans are shown in FIG. 9D, along with the distribution for interobserver differences of the averaged position of four markers.

Patient Studies

Figure 10:
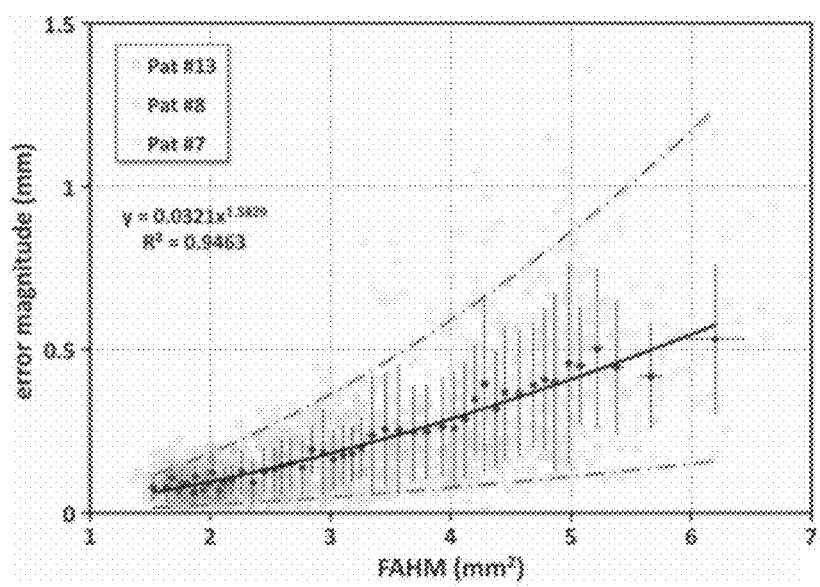
FIG. 10 is a plot of the full-areas-half-max (FAHM) and error magnitude for three patients.

Marker positions were manually tracked in three CBCT scans from three patients whose FAHM values span the range of values seen in this set of patients. FIG. 10 illustrates the relationship observed between FAHM and error magnitude for all three patients. With this relationship, FAHM values obtained during the automated tracking of patient data can be used to calculate inferred absolute error (IAE) values.

For all patients, the automated technique tracked marker clusters accurately in 100% of projections images wherein the entire cluster was visible, regardless of whether the templates used were static or dynamic. Beyond this tracking rate, Table I provides a patient-by-patient summary of four other noteworthy variables: (1) the number of markers in the cluster, (2) local maximum cross-correlation scores obtained during tracking, (3) global tracking rates, and (4) inferred absolute error values as calculated by FAHM values. All values shown in Table I were based on tracking that used dynamic templates, as they provided higher cross-correlation scores than static templates for select patients (discussed further below). Also, only projection images in which the entire marker cluster was visible in the field-of-view were considered for the data shown in Table I. The patients marked with "[a]" in Table I are the patients that have radio-opaque, nonmarker objects in the imaging plane. Patients #9 and #15 had migration events (see FIG. 12); as such, results are given as pre-/post-migration.

TABLE 1

Summary of metrics obtained for each patients using dynamic templates.

| patient # | # of markers | xcorr score ($\mu \pm \sigma$) | global tracking rate [%] | IAE ($\mu$, 90% range) [µm] |
|---|---|---|---|---|
| 1 | 4 | 0.79 ± 0.09 | 99.8 | 214, 128-283 |
| 2 | 3 | 0.86 ± 0.07 | 100 | 140, 44-206 |
| 3 | 2 | 0.78 ± 0.10 | 88.3 | 140, 31-210 |
| 4[a] | 3 | 0.71 ± 0.09 | 96.5 | 158, 31-206 |
| 5 | 4 | 0.84 ± 0.05 | 100 | 181, 89-193 |
| 6 | 3 | 0.80 ± 0.10 | 99.9 | 173, 89-268 |
| 7 | 4 | 0.48 ± 0.07 | 96.4 | 371, 268-459 |
| 8 | 3 | 0.88 ± 0.04 | 100 | 255, 128-369 |
| 9[a] | 2/1 | 0.51 ± 0.10/ 0.82 ± 0.15 | 66.0/77.0 | 118, 55-184/ 165, 102-231 |
| 10[a] | 3 | 0.76 ± 0.10 | 99.9 | 189, 102-274 |
| 11 | 3 | 0.79 ± 0.12 | 98.9 | 198, 136-259 |
| 12[a] | 4 | 0.57 ± 0.16 | 91.6 | 220, 65-313 |
| 13 | 4 | 0.83 ± 0.05 | 100 | 102, 65-136 |
| 14[a] | 3 | 0.60 ± 0.12 | 87.9 | 102, 44-170 |
| 15 | 3/3 | 0.91 ± 0.03/ 0.87 ± 0.05 | 100/99.1 | 193, 55-306/ 128, 44-200 |

Figure 11:
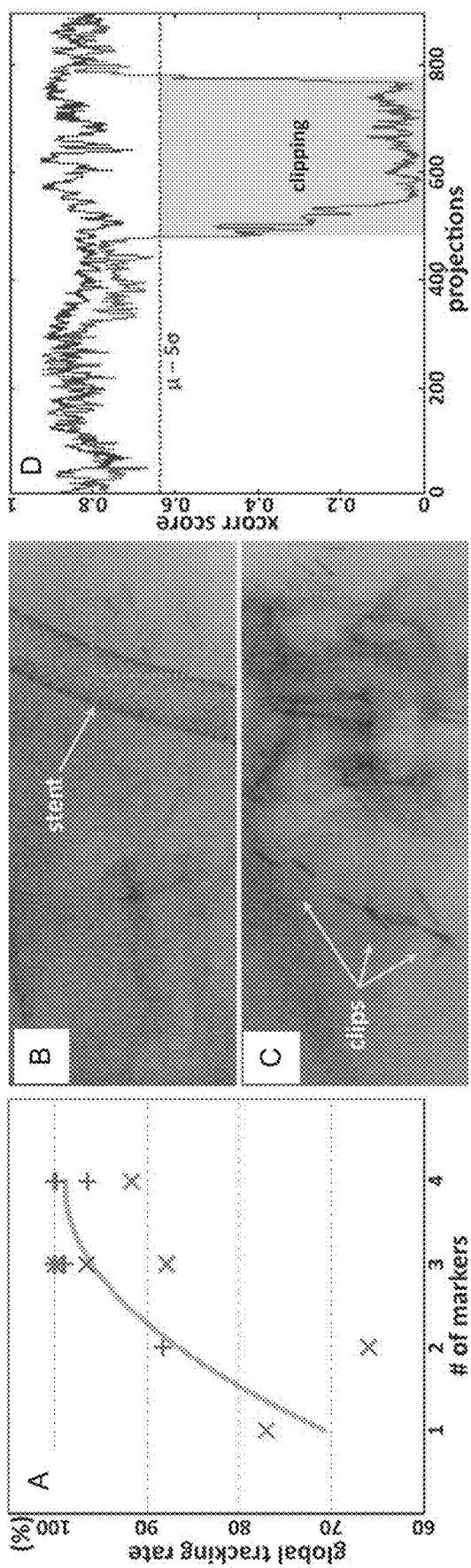
FIG. 11A is a plot of the global tracking rates with respect to the number of markers in the cluster.
FIGS. 11B-11C illustrate examples of radio-opaque non-marker objects that may be identified in various embodiments of the present technology.
FIG. 11D is a plot showing the cross-correlation scores for two fractions of the same patient.

Tracking metrics varied from patient-to-patient, but overall (I±r) cross-correlation scores were 0.76±0.12, global tracking rates were 94.9%±7.5%, and inferred absolute errors (I, 90% range) were 179 µm, 87-251 µm. Particularly noteworthy is the global tracking rate, because it provides an indication of the uniqueness of a cluster's appearance amongst the patient's anatomy and any foreign objects. FIG. 11A shows the relationship between global tracking rates with respect to the number of markers in the cluster. In accordance with some embodiments, increasing the number of markers in a cluster tends to increase the global tracking rate.

Cases with Radio-Opaque, Nonmarker Objects

For five patients, medical procedures prior to their radiation treatment resulted in other metallic objects being in the same imaging plane as their fiducial markers. Such objects can present serious challenges to tracking techniques that look for radio-opaque markers. In four of these patients (#4, #9, #12, and #14), the nonmarker object was a metallic biliary stent used to alleviate a blocked bile duct (see FIG. 11B). In one patient (#10), a large cluster of surgical clips was visible in the treatment plane (see FIG. 11C). Both of these object types pose unique challenges for any marker tracking technique. Metallic stents consist of a collapsible wire mesh that, once re-expanded, appears in projection images as a relatively large area of angled lines. Although, on their own, these stents are not likely to be confused for individual markers, markers can easily be camouflaged by stents whenever they overlap in projection images. Nevertheless, accurate tracking was maintained for all patients with biliary stents. The staples seen in FIG. 11C present an even bigger challenge for any technique that intends on tracking cylindrical markers. Despite the fact that these clips are quite similar in appearance to the markers being tracked, automated tracking was still successful, and the global tracking rate was an impressive 99.9%.

Various embodiments of the automatic template production performed well with both types of radio-opaque, nonmarker objects. For metallic stents, remnants of the wire mesh were apparent in the initial crude templates. However, the more predominant appearance of the marker cluster meant that subsequent iterations of tracking, stabilizing, and reconstructing end up homing in on the target marker cluster, and motion of the stent mesh relative to the cluster's position caused it to be blurred, falling below the '70% of maximum density threshold. In the case of the cluster of surgical clips, the cluster of clips was not included because it was too far from the isocenter to be considered in the template reconstruction volume. Hypothetically, if these clips were situated more closely to the target cluster, manual intervention might have been required to ensure that the clips were not included in the reconstructed cluster.

Cases with Insufficient Field-of-View

In 48 of the 75 CBCT scans examined, one or more markers moved outside the field-of-view during portions of the scan due to the lateral shift of the on-board imager that is imposed by a half-fan CBCT geometry. In some of these instances, tracking accuracy near the edge of the imager could be maintained by modifying templates based on the last known position of the cluster. When clusters moved near the edge of the field-of-view, some embodiments may crop templates 'on-the-fly' based on the proximity of the previously tracked position to the edge of the imaging panel (i.e., portions of the template occurring off of the imaging panel were set equal to zero).

As long as enough of the cluster remained visible—roughly half of the cluster—tracking could still be sustained in the phantom data. Such cropping allowed for more motion data to be salvaged from these clipped scans. A visual check of the stabilized scan was performed to verify the validity of tracking measurements in these cases. In 16 scans, more than half of the cluster fell outside the field-of-view at some point, and tracking of the cluster became either inaccurate or impossible at these positions. Nevertheless, by continuing to follow peaks at the edge of the imager, tracking was able to automatically resume accurately once the cluster returned into view in 13 of these 16 scans. In instances where portions of the cluster moved outside of the field-of-view, tracking could be resumed by once again finding the longest consecutive chain of global peaks in the subsequent set of projection images.

Analysis of these events helped to provide some insight into how tracking failures might be recognized when using the current technique. For these cases, tracking was repeated without implementing the template cropping technique described above. When clipping occurred, significant drops in cross-correlation scores were observed. An example of this is shown in FIG. 11D, with the clipping event corresponding exceptionally well with the portion of the scan where cross-correlation scores dropped more than five standard deviations below the mean score observed in another scan from the same patient in which a clipping event did not occur. Due to the range of average cross-correlation scores seen in individual patients, it is likely that a single threshold value would not be suitable for catching detection errors for all patients. Instead, statistically significant drops in cross-correlation scores for each patient would be more appropriate. If one can determine the point at which a cluster has been lost from the field-of-view, one could continue to monitor the last known position of the cluster instead of following peaks at the edge of the imager, potentially improving the technique's ability to resume tracking after.

Cases with Marker Migration

Three patients had noticeable marker migration events. One patient (#3) had a marker dislodge prior to their first radiation treatment, resulting in two markers remaining in place and the dislodged marker visibly loose in the patient's abdominal cavity. One patient (#9) had one marker dislodge before the first treatment fraction, and a second marker dislodge after the first fraction, resulting in only one marker remaining in place for the last four fractions. One patient (#15) had one of three markers noticeably shift its position relative to other markers after three treatment fractions. Patients #9 and #15, having had CBCT scans before and after a migration event, served as useful cases to evaluate how robust the current technique would be against marker migration. As such, marker clusters were tracked in post-migration CBCT scans in accordance with some embodiments that use two different sets of dynamic templates: templates produced from images obtained on the treatment day prior to the migration event (premigration templates), and templates produced from images obtained on the treatment day after the migration event (postmigration templates). With the assumption that postmigration templates would more accurately track marker clusters in the postmigration scan, the difference between these two motion measurements would be indicative of the magnitude of errors one could expect if new templates were not produced after a migration event.

Figure 12:
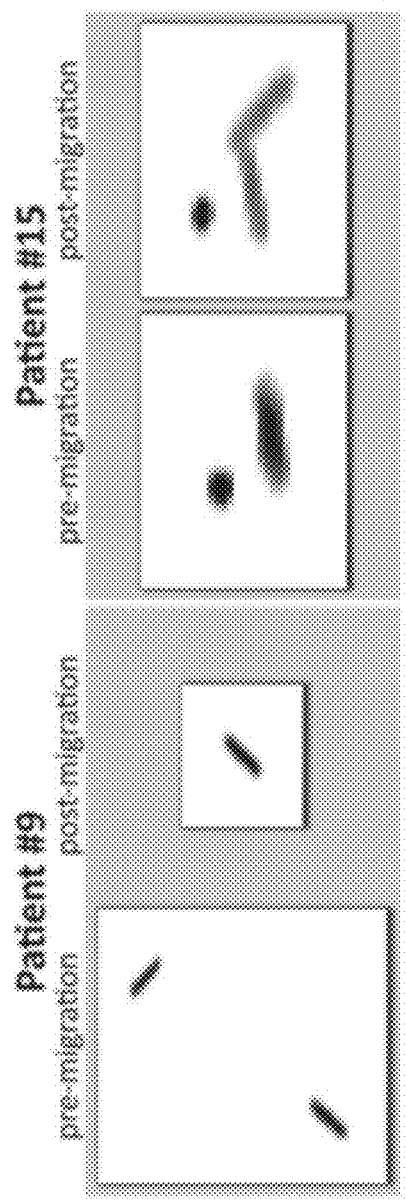
FIG. 12 shows examples of noticeable marker migration between treatment fractions of two patients.

Premigration and postmigration templates for patients #9 and #15 are shown in FIG. 12. In the case where premigration templates were used to track motion in the postmigration scan, tracking was still successfully automated. After correcting for differences in the centroid positions of pre- and postmigration templates, the maximum difference between positions tracked by pre- and postmigration templates was 203 µm for patient #9, and 91 µm for patient #15.

Static Templates Vs. Dynamic Templates

Figure 13:
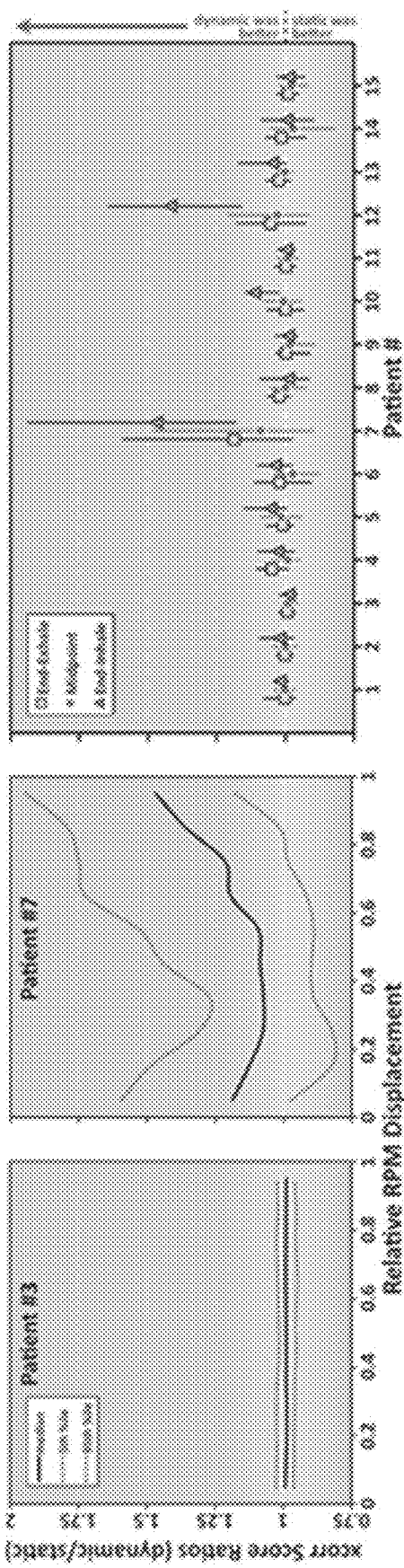
FIG. 13 shows the ratios of cross-correlation scores obtained using either dynamic or static templates created according to various embodiments of the present technology.

Most patients saw little difference in their cross-correlation scores when dynamic templates were used instead of static templates. FIG. 13 provides a summary of cross-correlation score ratios (dynamic/static), with ratios greater than 1 indicating that higher cross-correlation scores were obtained by dynamic templates. Sample plots of score ratios with respect to relative RPM displacement are shown for patient #3 and patient #7, the patients benefiting the least and the most from dynamic templates, respectively. End-exhalation, midpoint, and end-inhalation points are plotted for all patients.

Patient #7 and patient #12 both benefited significantly from dynamic templates, with patient #7's cluster exhibiting considerable deformation during their breathing cycle, and patient #12's cluster exhibiting considerable rotation. For these two patients, the highest benefit when using dynamic templates was seen in end-inhalation phases, which is to be expected. Static templates represent an average of the cluster's appearance throughout the breathing cycle. With more time being spent in end-exhalation and mid-range phases, static templates tend to be more representative of the cluster during those intervals. Dynamic templates allow for images to be prepared that are more representative of the cluster throughout all phases of the breathing cycle. Although the majority of patients did not exhibit levels of deformation or rotation that necessitated the use of dynamic templates, it should be noted that the use of dynamic templates did not have a detrimental effect on cross-correlation scores for these patients. As such, in a clinical scenario where breathing data were available, dynamic templates could be used by default for all patients.

The majority of errors observed in the phantom study were less than 100 µm. Maximum errors for the 0D and 1D scans were smaller than the width of a single pixel, and the maximum error for the 3D scan was smaller than the width of two pixels. By demonstrating sub-pixel accuracy, these studies support the choice to use the centroid of 9 pixels with the highest cross-correlation scores to determine the position of the cluster used in some embodiments. Furthermore, this shows that, template matching techniques can be implemented in ways that allow for sub-pixel precision. Had the current work been implemented based on single pixel position measurements, possible positions would have been limited to a grid with 259 µm between points, and errors would have been significantly larger as a result.

As for accuracy in patient studies, the relationship observed between FAHM and inferred absolute error offers a new metric for monitoring accuracy in cases where the ground truth is unknown. 14 out of 15 patients had an average inferred absolute error smaller than the width of a single pixel, which is especially impressive when one considers how imprecise human measurements are known to be. Results from the phantom study showed that distributions of inter and intraobserver differences were wider than error distributions obtained by the automated tracking routine. As such, FAHM can be used to monitor the sharpness of cross-correlation peaks used in some embodiments for monitoring the accuracy of real-time template matching techniques.

The values observed for global tracking rate highlight the importance of the local tracking window. An ideal rate of 100% would indicate that the performance of the technique was not reliant on restricting the search to the local window. Otherwise, the size of the local window becomes increasingly important as imaging frequency decreases. A 21×21 local window used in some embodiments may be small enough to maintain accurate tracking for all images, yet large enough to observe the maximum interframe shifts observed: 6.72 and 6.91 pixels in lateral and superior-inferior directions, respectively. If imaging frequency were reduced, these maximum interframe shift values would increase, which could require an increase in the size of the local window. As such, tracking techniques should strive to produce maxima that maintain their maximum status beyond the local window. High global tracking rates are dependent on the target's appearance being distinct in comparison to other aspects of the projection image. Many parts of a patient's anatomy can easily be confused for a single marker, especially when the marker is spherical or cylindrical. Detection of false markers is a widespread issue when tracking markers individually, which calls for the use of elaborate methods of rejecting false markers. Various embodiments seek the entire cluster as a single entity produces templates that are much more distinct.

The version of the algorithm implemented in the phantom study was not optimized for speed. Beginning with raw projection images, automated target tracking and dynamic template production for a single CBCT scan was performed in 30 minutes to an hour on a desktop personal computer (64-bit Windows 7, Intel Core i7-6700 CPU, 3.40 GHz, 16 GB RAM). If one sought to use this technique simply to obtain target motion data, this speed is already more than sufficient and could be executed on a computer outside of the clinical workflow. In order to immediately prepare templates for tracking targets in intrafractional kV images, the speed of the algorithm would need to be improved. However, if templates are prepared ahead of time, intrafractional tracking is feasible.

Some parameters described above were reached empirically. While these parameters would remain stable for a given anatomic site and imaging technique, the parameters may need to be adjusted to accommodate other scenarios. For projection images with larger amounts of noise, the size of filtering neighborhoods used in the initial image processing step may need to be increased. For other marker materials, the density threshold used to clean up the reconstructed cluster volume may need to be adjusted.

Exemplary Computer System Overview

Aspects and implementations of the automated target tracking system of the disclosure have been described in the general context of various steps and operations. A variety of these steps and operations may be performed by hardware components or may be embodied in computer-executable instructions, which may be used to cause a general-purpose or special-purpose processor (e.g., in a computer, server, or other computing device) programmed with the instructions to perform the steps or operations. For example, the steps or operations may be performed by a combination of hardware, software, and/or firmware.

Figure 14:
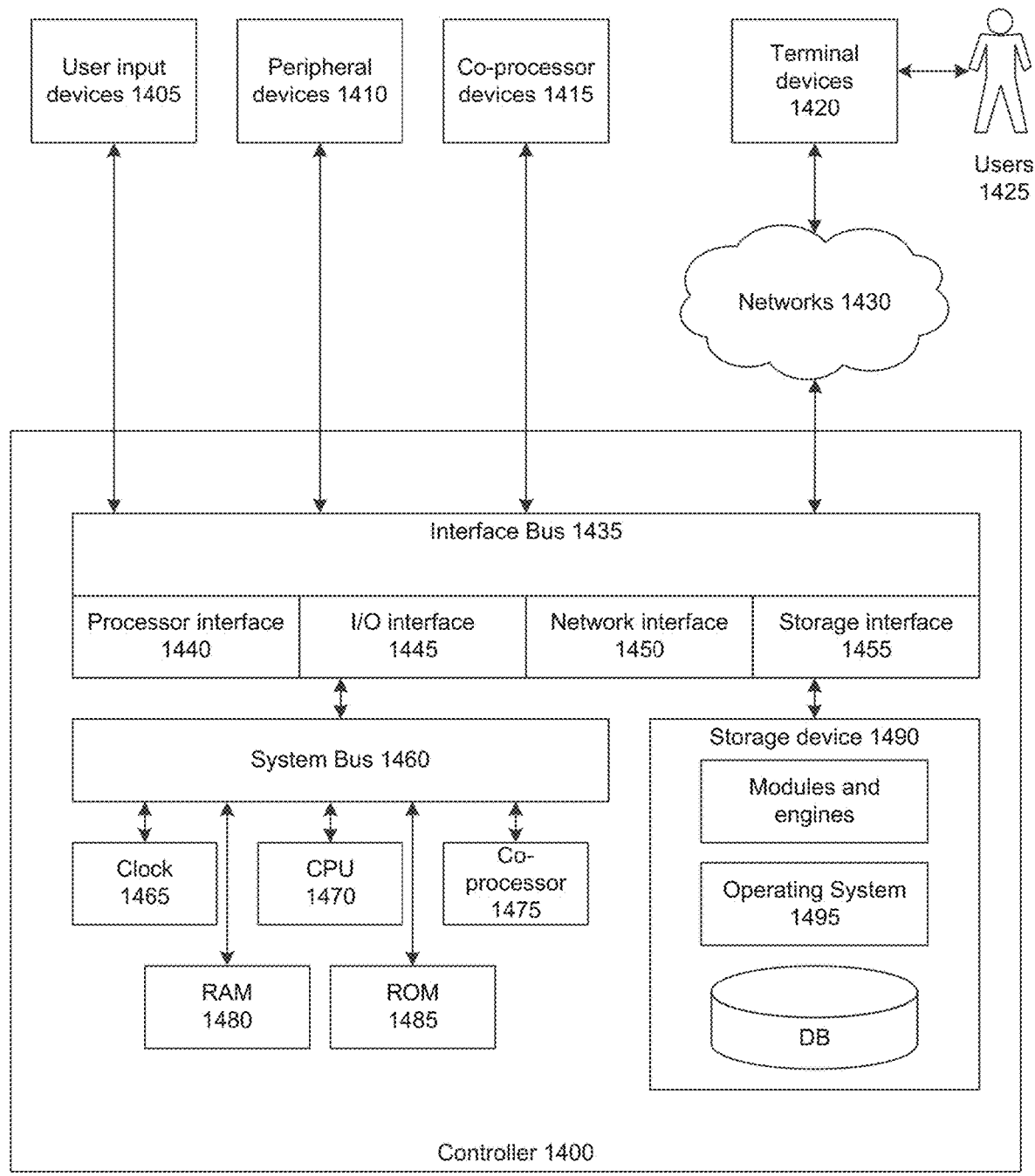
FIG. 14 is an example of a computing system that may be used in accordance with one or more embodiments of the present technology.

FIG. 14 is a block diagram illustrating an example machine representing the computer systemization of the automated tracking system. The automated tracking system controller may be integrated into medical devices or a separate device that is in communication with one or more medical devices. The automated tracking system controller 1400 may be in communication with entities including one or more users 1425 client/terminal devices 1420, user input devices 1405, peripheral devices 1410, an optional co-processor device(s) (e.g., cryptographic processor devices) 1415, and networks 1430. Users may engage with the controller 1400 via terminal devices 1420 over networks 1430.

Computers may employ central processing unit (CPU) or processor to process information. Processors may include programmable general-purpose or special-purpose microprocessors, programmable controllers, application-specific integrated circuits (ASICs), programmable logic devices (PLDs), embedded components, combination of such devices and the like. Processors execute program components in response to user and/or system-generated requests. One or more of these components may be implemented in software, hardware or both hardware and software. Processors pass instructions (e.g., operational and data instructions) to enable various operations.

The controller 1400 may include clock 1465, CPU 1470, memory such as read only memory (ROM) 1485 and random-access memory (RAM) 1480 and co-processor 1475 among others. These controller components may be connected to a system bus 1460, and through the system bus 1460 to an interface bus 1435. Further, user input devices 1405, peripheral devices 1410, co-processor devices 1415, and the like, may be connected through the interface bus 1435 to the system bus 1460. The interface bus 1435 may be connected to a number of interface adapters such as processor interface 1440, input output interfaces (I/O) 1445, network interfaces 1450, storage interfaces 1455, and the like.

Processor interface 1440 may facilitate communication between co-processor devices 1415 and co-processor 1475. In one implementation, processor interface 1440 may expedite encryption and decryption of requests or data. Input output interfaces (I/O) 1445 facilitate communication between user input devices 1405, peripheral devices 1410, co-processor devices 1415, and/or the like and components of the controller 1400 using protocols such as those for handling audio, data, video interface, wireless transceivers, or the like (e.g., Bluetooth, IEEE 1394a-b, serial, universal serial bus (USB), Digital Visual Interface (DVI), 802.11a/b/g/n/x, cellular, etc.). Network interfaces 1450 may be in communication with the network 1430. Through the network 1430, the controller 1400 may be accessible to remote terminal devices 1420. Network interfaces 1450 may use various wired and wireless connection protocols such as, direct connect, Ethernet, wireless connection such as IEEE 802.11a-x, and the like.

Examples of network 1430 include the Internet, Local Area Network (LAN), Metropolitan Area Network (MAN), a Wide Area Network (WAN), wireless network (e.g., using Wireless Application Protocol WAP), a secured custom connection, and the like. The network interfaces 1450 can include a firewall which can, in some aspects, govern and/or manage permission to access/proxy data in a computer network, and track varying levels of trust between different machines and/or applications. The firewall can be any number of modules having any combination of hardware and/or software components able to enforce a predetermined set of access rights between a particular set of machines and applications, machines and machines, and/or applications and applications, for example, to regulate the flow of traffic and resource sharing between these varying entities. The firewall may additionally manage and/or have access to an access control list which details permissions including, for example, the access and operation rights of an object by an individual, a machine, and/or an application, and the circumstances under which the permission rights stand. Other network security functions performed or included in the functions of the firewall, can be, for example, but are not limited to, intrusion-prevention, intrusion-detection, next-generation firewall, personal firewall, etc., without deviating from the novel art of this disclosure.

Storage interfaces 1455 may be in communication with a number of storage devices such as, storage devices 1490, removable disc devices, and the like. The storage interfaces 1455 may use various connection protocols such as Serial Advanced Technology Attachment (SATA), IEEE 1394, Ethernet, Universal Serial Bus (USB), and the like.

User input devices 1405 and peripheral devices 1410 may be connected to I/O interface 1445 and potentially other interfaces, buses and/or components. User input devices 1405 may include card readers, finger print readers, joysticks, keyboards, microphones, mouse, remote controls, retina readers, touch screens, sensors, and/or the like. Peripheral devices 1410 may include antenna, audio devices (e.g., microphone, speakers, etc.), cameras, external processors, communication devices, radio frequency identifiers (RFIDs), scanners, printers, storage devices, transceivers, and/or the like. Co-processor devices 1415 may be connected to the controller 1400 through interface bus 1435, and may include microcontrollers, processors, interfaces or other devices.

Computer executable instructions and data may be stored in memory (e.g., registers, cache memory, random access memory, flash, etc.) which is accessible by processors. These stored instruction codes (e.g., programs) may engage the processor components, motherboard and/or other system components to perform desired operations. The controller 1400 may employ various forms of memory including on-chip CPU memory (e.g., registers), RAM 1480, ROM 1485, and storage devices 1490. Storage devices 1490 may employ any number of tangible, non-transitory storage devices or systems such as fixed or removable magnetic disk drive, an optical drive, solid state memory devices and other processor-readable storage media. Computer-executable instructions stored in the memory may include the automated tracking platform 1420 having one or more program modules such as routines, programs, objects, components, data structures, and so on that perform particular tasks or implement particular abstract data types. For example, the memory may contain operating system (OS) component 1495, modules and other components, database tables, and the like. These modules/components may be stored and accessed from the storage devices, including from external storage devices accessible through an interface bus.

The database components can store programs executed by the processor to process the stored data. The database components may be implemented in the form of a database that is relational, scalable and secure. Examples of such database include DB2, MySQL, Oracle, Sybase, and the like. Alternatively, the database may be implemented using various standard data-structures, such as an array, hash, list, stack, structured text file (e.g., XML), table, and/or the like. Such data-structures may be stored in memory and/or in structured files.

The controller 1400 may be implemented in distributed computing environments, where tasks or modules are performed by remote processing devices, which are linked through a communications network, such as a Local Area Network ("LAN"), Wide Area Network ("WAN"), the Internet, and the like. In a distributed computing environment, program modules or subroutines may be located in both local and remote memory storage devices. Distributed computing may be employed to load balance and/or aggregate resources for processing. Alternatively, aspects of the controller 1400 may be distributed electronically over the Internet or over other networks (including wireless networks). Those skilled in the relevant art(s) will recognize that portions of the automated tracking system may reside on a server computer, while corresponding portions reside on a client computer. Data structures and transmission of data particular to aspects of the controller 1400 are also encompassed within the scope of the disclosure.

In the attached Appendices, illustrative embodiments of the systems and methods are described and set forth. These illustrations are not intended to be exhaustive or limiting, but rather to highlight some of the features, benefits and advantages associated with various embodiments of the technology.

CONCLUSION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

What is claimed is:

1. A method comprising:
   receiving multiple projection images collected using a cone beam computed tomography (CBCT) scan of a patient having a cluster of fiducial markers;
   generating filtered marker enhanced images from the multiple projection images using one or more filters;
   generating a three-dimensional volume reconstruction by applying a filtered back projection on the filtered marker enhanced images;
   applying a forward projection to the three-dimensional volume reconstruction to create a set of static image templates; and
   stabilizing, using the set of static image templates, the filtered marker enhanced images to produce stabilized filtered marker enhanced images.

2. The method of claim 1, further comprising:
   generating a second three-dimensional volume reconstruction by applying the filtered back projection on the stabilized filtered marker enhanced images;
   applying a forward projection to the second three-dimensional volume reconstruction to create a second set of static image templates; and
   stabilizing, using the second set of static image templates, the filtered marker enhanced images to produce a second set of stabilized filtered marker enhanced images.

3. The method of claim 1, further comprising:
   generating a four-dimensional volume reconstruction by reconstructing sets of projection data binned according to different phases of a breathing cycle of the patient; and
   applying a forward projection to the four-dimensional volume reconstruction to create a set of dynamic templates.

4. The method of claim 1, further comprising:
   automatically searching for the cluster of fiducial markers within the stabilized filtered marker enhanced images; and
   applying a treatment beam to an area around the cluster of fiducial markers.

5. The method of claim 4, wherein automatically searching for the cluster of fiducial markers includes:
   generating a set of templates isolating the cluster of fiducial markers; and
   compensating for movement of the patient.

6. The method of claim 5, wherein compensating for movement of the patient includes using gating information based on a breathing pattern of the patient.

7. The method of claim 1, wherein the one or more filters include a median image filter.

8. The method of claim 1, further comprising:
   monitoring for migration any fiducial marker within the cluster of fiducial markers over a period of time; and
   generating, upon detection of migration of any fiducial marker within the cluster of fiducial markers, an updated set of static image templates.

9. A method comprising:
   receiving multiple projection images of a patient having a cluster of fiducial markers;
   searching the multiple projection images for the cluster of fiducial markers;
   generating a set of templates isolating the cluster of fiducial markers; and
   cross-correlating the set of templates and the multiple projection images in a template matching process.

10. The method of claim 9, wherein the receiving includes receiving the multiple projection images from a cone beam computed tomography (CBCT) scan.

11. The method of claim 9 further comprising generating filtered marker enhanced images from the multiple projection images using one or more filters.

12. The method of claim 11 further comprising generating a three-dimensional volume reconstruction by applying a filtered back projection on the filtered marker enhanced images.

13. The method of claim 9 further comprising creating final stabilized filtered marker images by repeating the following steps multiple times:
   applying a forward projection to the three-dimensional volume reconstruction to create a set of static image templates;
   stabilizing, using gating information collected during the CBCT scan and the set of static image templates, the filtered marker enhanced images to produce stabilized filtered marker enhanced images; and
   applying an additional filtered back projection to the stabilized filtered marker enhanced images to update the three-dimensional volume reconstruction.

14. The method of claim 13, wherein compensating for movement of the patient includes using gating information based on a breathing pattern of the patient.

15. The method of claim 9 further comprising applying, upon identification of the cluster of fiducial markers, a treatment beam to the patient.

16. The method of claim 9, wherein the searching further includes compensating for movement of the patient.

17. The method of claim 15, wherein compensating for movement of the patient includes using gating information based on a breathing pattern of the patient.

18. A system comprising:
a communications interface configured to receive multiple projection images of a patient having a cluster of fiducial markers; and
at least one processor coupled to the communications interface, and configured to:
search the multiple projection images for the cluster of fiducial markers;
generate a set of templates isolating the cluster of fiducial markers; and
cross-correlate the set of templates and the multiple projection images in a template matching process.

19. The system of claim 18, wherein the at least one processor is further configured to:
generate filtered marker enhanced images from the multiple projection images using one or more filters;
generate a three-dimensional volume reconstruction by applying a filtered back projection on the filtered marker enhanced images; and
apply a forward projection to the three-dimensional volume reconstruction to create a set of static image templates.

20. The system of claim 19, wherein the at least one processor is further configured to stabilize, using the set of static image templates, the filtered marker enhanced images to produce stabilized filtered marker enhanced images.

21. The system of claim 18, wherein the at least one processor is further configured to cause, upon identification of the cluster of fiducial markers, a treatment beam to be applied to the patient.

22. The system of claim 18 further comprising an imaging device to scan the patient and collect the multiple projection images.

23. The system of claim 22, wherein the imaging device includes; a cone beam computed tomography (CBCT) device, a C-arm computed tomography scanner, or a fluoroscopy machine.

24. The system of claim 18, wherein to search the multiple projection images for the cluster of fiducial markers, the at least one processor is further configured to compensate for movement of the patient based on gating information collected from the multiple projection images.

* * * * *

UNITED STATES PATENT AND TRADEMARK OFFICE
CERTIFICATE OF CORRECTION

| | | |
|---|---|---|
| PATENT NO. | : 11,253,210 B2 | Page 1 of 1 |
| APPLICATION NO. | : 15/662925 | |
| DATED | : February 22, 2022 | |
| INVENTOR(S) | : Bernard Jones et al. | |

It is certified that error appears in the above-identified patent and that said Letters Patent is hereby corrected as shown below:

On the Title Page

Item (72) delete "Mitten" and insert --Miften--

Signed and Sealed this
Third Day of October, 2023

Katherine Kelly Vidal
*Director of the United States Patent and Trademark Office*